US009717395B2

(12) United States Patent
Toyoda

(10) Patent No.: US 9,717,395 B2
(45) Date of Patent: Aug. 1, 2017

(54) SUCTION CONDUIT SWITCHING APPARATUS AND ENDOSCOPE

(71) Applicant: FUJIFILM Corporation, Tokyo (JP)

(72) Inventor: Yusuke Toyoda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 306 days.

(21) Appl. No.: 14/613,138

(22) Filed: Feb. 3, 2015

(65) Prior Publication Data

US 2015/0216394 A1    Aug. 6, 2015

(30) Foreign Application Priority Data

Feb. 6, 2014  (JP) ................................. 2014-021781

(51) Int. Cl.
| | |
|---|---|
| *A61B 1/00* | (2006.01) |
| *A61B 1/015* | (2006.01) |
| *F16K 11/07* | (2006.01) |
| *A61B 1/04* | (2006.01) |

(52) U.S. Cl.
CPC ...... *A61B 1/00068* (2013.01); *A61B 1/00094* (2013.01); *A61B 1/00119* (2013.01); *A61B 1/00128* (2013.01); *A61B 1/015* (2013.01); *F16K 11/0716* (2013.01)

(58) Field of Classification Search
CPC . A61B 1/00068; A61B 1/015; A61B 1/00128; A61B 1/00119; A61B 1/00094; F16K 11/0716
See application file for complete search history.

(56) References Cited

FOREIGN PATENT DOCUMENTS

| | | |
|---|---|---|
| CN | 203074661 U | 7/2013 |
| DE | 102004003857 A1 | 8/2004 |
| DE | 102009014050 A1 | 9/2010 |
| JP | 7-8448 A | 1/1995 |
| JP | 8-21551 A | 1/1996 |
| JP | 2000-189380 A | 7/2000 |

(Continued)

OTHER PUBLICATIONS

Translation, Mitsumori DE102004003857, 11 pages.*

(Continued)

*Primary Examiner* — Timothy J Neal
(74) *Attorney, Agent, or Firm* — Birch, Stewart & Kolasch & Birch, LLP

(57) ABSTRACT

A piston is inserted into a piston passage of a cylinder. The piston is displaced between a first position of a non-contact state and a second position by a pressing operation. At the first position, a suction source connection port of the cylinder faces a circumferential groove of the piston and a suction source conduit communicates with an outside atmosphere. At the second position, the suction source connection port faces an outer peripheral surface opening and the suction source conduit communicates with a suction connection port. A V-shaped opening portion as a correction opening portion is formed in the outer peripheral surface opening. The V-shaped opening portion causes an increment of a communication opening width at which the suction source connection port overlaps with the outer peripheral surface opening to be three times or less an increment of a pressing stroke of the piston.

12 Claims, 13 Drawing Sheets

(56) References Cited

FOREIGN PATENT DOCUMENTS

JP        2004-223121 A      8/2004

OTHER PUBLICATIONS

Japanese Office Action for Japanese Application No. 2014-021781, dated Jan. 6, 2016, with an English translation.
Extended European Search Report for European Application No. 15152714.0, dated May 28, 2015.
Chinese Office Action and Search Report dated Mar. 20, 2017, for Chinese Application No. 201510013197.7, with an English translation of the Office Action only.

* cited by examiner

SUCTION CONDUIT SWITCHING APPARATUS AND ENDOSCOPE

CROSS-REFERENCE TO RELATED APPLICATIONS

The present application claims priority under 35 U.S.C. §119 to Japanese Patent Application No. 2014-021781, filed on Feb. 6, 2014. Each of the above application(s) is hereby expressly incorporated by reference, in its entirety, into the present application.

BACKGROUND OF THE INVENTION

1. Field of the Invention

The claimed invention relates to a suction conduit switching apparatus for an endoscope that switches a conduit from a suction port at a tip of an endoscope insertion section and an endoscope.

2. Description of the Related Art

An endoscope is provided with a suction conduit that leads to a suction port at a tip in an insertion section which is inserted into a body of a patient. The suction conduit is connected to a suction conduit switching apparatus that is disposed in a hand operation unit. The suction conduit is also used as a treatment tool insertion channel that is used to insert a treatment tool such as a forceps. The suction conduit that branches from the middle of the treatment tool insertion channel is connected to the suction conduit switching apparatus in most cases.

A suction source conduit that leads to a suction source such as a suction pump and the suction conduit are connected to the suction conduit switching apparatus. Switching between a stand-by state where the suction source conduit and the suction conduit are blocked and a suctioning state where the suction source conduit and the suction conduit communicate with each other to allow suctioning can be performed by a pressing operation.

The suction conduit switching apparatus, examples of which include a suction button, is provided with a cylinder and a piston. In suction buttons in JP1995-008448A (JP-H07-008448A) and JP2004-223121A, a cylinder has a piston passage that has one open end, a suction connection port that is formed at the other end of the piston passage and leads to a suction conduit, and a suction source connection port that is formed in an inner peripheral surface of the piston passage and leads to a suction source conduit. A piston is inserted into the piston passage from the other end and is displaced from a first position to a second position by a pressing operation. An outer peripheral surface opening that communicates with the suction source connection port at the second position, the other end opening that is formed at the other end and communicates with the suction connection port, and a communication passage that allows the outer peripheral surface opening and the other end opening to communicate with each other are formed in the piston. When the piston is moved to the second position by pressing an operation cap that is fixed to the piston and the outer peripheral surface opening of the piston is allowed to communicate with the suction source connection port of the cylinder, the suction conduit and the suction source conduit communicate with each other and suctioning from a suction port is performed.

In an endoscope apparatus in JP2000-189380A, a suction amount is controlled in response to an operation cap pressing amount. According to JP2000-189380A, a rotation valve is subjected to rotation control via a motor so that a leak hole of a leak valve is closed by a predetermined amount and the suction amount is controlled or a rotating roller is subjected to rotation control. In this manner, pressing of a suction tube by a suction roller and a suction tube pressure plate is gradually opened so that the suction amount is controlled.

SUMMARY OF THE INVENTION

According to JP1995-008448A (JP-H07-008448A), both ends of both the suction source connection port of the cylinder and the outer peripheral surface opening of the piston are arc-shaped long holes. According to JP2004-223121A, both ends of both the suction source connection port of the cylinder and the outer peripheral surface opening of the piston have a circular shape. For operability improvement, it is preferable that the suction amount linearly increase with respect to the pressing amount of the piston. However, in a case where a part where the suction source connection port and the outer peripheral surface opening start communicating with each other is arc-shaped as in each of JP1995-008448A (JP-H07-008448A) and JP2004-223121A, the suction amount rapidly increases with respect to the pressing amount of the piston at the part where both the suction source connection port and the outer peripheral surface opening start communicating with each other. In a case where air supply or water supply into the body is performed, an operator performs suctioning at the same time by half-pressing the operation cap so as to perform control for preventing air and a liquid from remaining in the body. However, it is difficult to set a desired suction amount if the part where the suction amount rapidly increases with respect to the pressing amount of the piston is present.

According to JP2000-189380A, the suction amount is electrically controlled so that the rapid change in suction amount can be prevented. However, the electrical and complicated control for controlling the suction amount adds to the complexity of the apparatus, increases the number of components, and increases costs unlike in mechanical control of the suction amount using communication between the suction source connection port of the cylinder and the outer peripheral surface opening of the piston.

The claimed invention has been made in view of the above problems, and an objective thereof is to provide a suction conduit switching apparatus for an endoscope capable of preventing a rapid increase in suction amount with respect to a pressing amount of a piston by using a simple configuration and an endoscope.

A suction conduit switching apparatus for an endoscope according to an aspect of the claimed invention includes a cylinder, a piston, a first communication passage, a second communication passage, and a rotation regulating unit. The cylinder is disposed in a hand operation unit of the endoscope and has a piston passage, a suction connection port, and a suction source connection port. One end of the piston passage is open and the piston is inserted from the one end. The suction connection port is formed at the other end of the piston passage and leads to a suction conduit. The suction source connection port is formed in an inner peripheral surface of the piston passage and leads to a suction source conduit. The one end of the piston that is inserted into the cylinder protrudes from the piston passage. The piston is displaced from a first position to a second position by a pressing operation. The first communication passage has an outer peripheral surface opening and the other end opening and allows the outer peripheral surface opening and the other end opening to communicate with each other. The outer peripheral surface opening is formed in an outer peripheral surface of the piston, communicates with the suction source connection port when the piston is at the second position, and is blocked by the inner peripheral surface of the piston passage when the piston is at the first position. The other end opening is formed at the other end of the piston and communicates with the suction connection port. The second communication passage has a circumferential groove and a notch passage and allows the suction source connection port to communicate with an outside atmosphere via the circumferential groove and the notch passage. The circumferential groove is formed in the outer peripheral surface of the piston, communicates with the suction source connection port when the piston is at the first position, and is blocked by the inner peripheral surface of the piston passage when the piston is at the second position. The notch passage is formed from the circumferential groove to the one end of the piston in the outer peripheral surface of the piston. The rotation regulating unit regulates rotation of the piston in the piston passage. When the piston is displaced from the first position to the second position by the pressing operation to the one end of the piston, an increase of a communication opening width at which the suction source connection port and the outer peripheral surface opening overlap with each other is equal to or less than three times an increment of a pressing stroke of the piston.

The increment of the communication opening width may be equal to or more than 1.0 times and equal to or less than 2.5 times the increment of the pressing stroke of the piston when the piston is displaced from the first position to the second position by the pressing operation to the one end of the piston.

At least one of the suction source connection port and the outer peripheral surface opening may have a correction opening portion that has an opening width gradually increasing from the other end side toward the one end side. One of the suction source connection port and the outer peripheral surface opening may have a rectangular shape and the other one may have a V-shaped correction opening portion at a part starting communicating with the one of the suction source connection port and the outer peripheral surface opening in response to pressing of the piston. The other one may have an arc-shaped opening portion continuing from the correction opening portion. The outer peripheral surface opening may be smaller than the suction source connection port.

An inclined notch that continues from the circumferential groove on the other end side rather than the circumferential groove, communicates with the suction source connection port at the first position, and faces the inner peripheral surface of the piston passage at the second position may be formed in the outer peripheral surface of the piston. The inclined notch may be formed in a direction in which a suction source connection passage that communicates with the suction source connection port extends.

The suction conduit switching apparatus for an endoscope may further include a cylinder cap, an operation cap, and a spring. The cylinder cap may be mounted on the cylinder and regulates separation of the piston from the one end of the piston passage. The operation cap may be disposed at the one end of the piston. The spring may be disposed between the operation cap and the cylinder cap and biases the piston toward the cylinder cap. The piston may be stationary at the first position as abutting against the cylinder cap and due to the biasing by the spring. The piston may be stationary at the second position with the operation cap that is pushed down against the biasing by the spring abutting against the cylinder cap.

The endoscope according to an aspect of the claimed invention includes the suction conduit switching apparatus for an endoscope, an insertion section, a hand operation unit, a suction source conduit, and a suction conduit. The insertion section is inserted into a body. The hand operation unit is disposed to be connected to the insertion section. The suction source conduit is connected to a suction source. The suction conduit communicates with a suction port that is disposed in the insertion section.

According to the aspects of the claimed invention, the increment of the communication opening width at which the suction source connection port and the outer peripheral surface opening overlap with each other is three times or less the increment of the pressing stroke of the piston when the piston is displaced, and thus a rapid increase of the communication opening width can be prevented. Accordingly, a rapid increase in suction amount with respect to the pressing amount of the piston can be prevented and the suction amount can be decreased in a half-pressing state.

DESCRIPTION OF THE PREFERRED EMBODIMENTS

Figure 1:
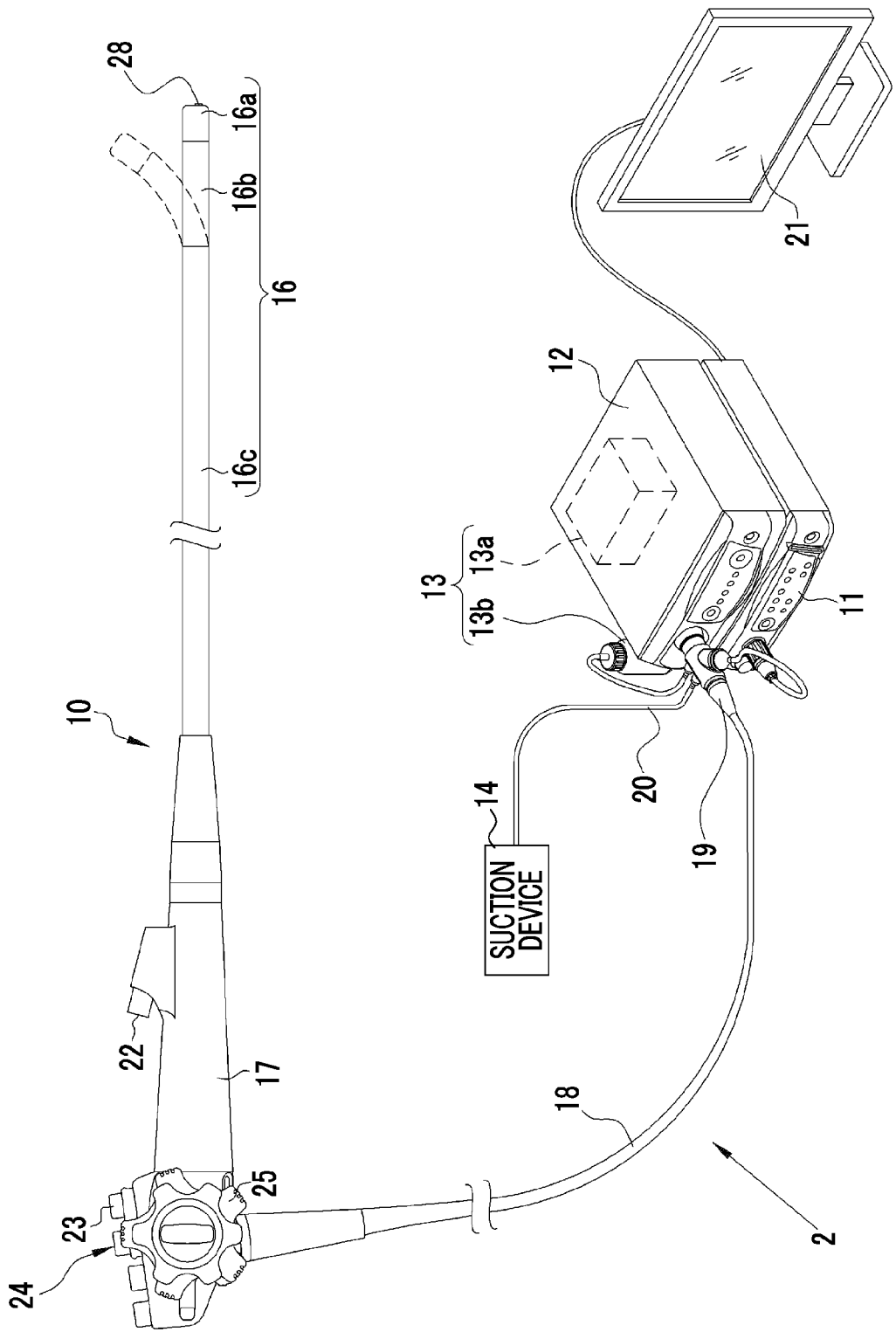
FIG. 1 is an external perspective view of an endoscope system.

As illustrated in FIG. 1, an endoscope system 2 is provided with an electronic endoscope 10, a processor device 11, a light source device 12, an air/water supply device 13, and a suction device 14. The air/water supply device 13 is built into the light source device 12, and has a known air supply device (pump or the like) 13a that performs gas supply and a wash water tank 13 that is disposed out of the light source device 12 and stores wash water. The electronic endoscope 10 has a flexible insertion section 16 that is inserted into a body, a hand operation unit 17 that is disposed to be connected to a proximal end part of the insertion section 16, and a universal cord 18 that is connected to the processor device 11 and the light source device 12.

The insertion section 16 has, in order from a tip, a tip portion 16a, a bending portion 16b, and a flexible pipe unit 16c. A camera unit 43 (refer to FIG. 2) that is used in internal imaging of the body of a patient is built into the tip portion 16a. The bending portion 16b is disposed to be connected to a proximal end of the tip portion 16a and is configured to be bendable. The flexible pipe unit 16c is disposed to be connected to a proximal end of the bending portion 16b and has flexibility.

A connector 19 is mounted on a tip of the universal cord 18. The connector 19 is a complex-type connector, and each of the processor device 11, the light source device 12, and the air/water supply device 13 is connected to the connector 19. The suction device 14 is connected to the connector 19 via a connecting tube 20.

The processor device 11 is electrically connected to the light source device 12 and performs overall control on an operation of the endoscope system 2. The processor device 11 performs electric power supply to the electronic endoscope 10 via a transmission cable that is built into the universal cord 18 and the insertion section 16 and controls driving of the camera unit 43. The processor device 11 acquires an imaging signal that is output from the camera unit 43 via the transmission cable and generates image data by performing various types of image processing. The image data generated by the processor device 11 is displayed as an observation image on a monitor 21 that is cable-connected to the processor device 11.

A treatment tool inlet 22, an air/water supply button 23, a suction button 24 as a suction conduit switching apparatus for the endoscope, a bending operation knob 25, and the like are disposed in the hand operation unit 17. When the bending operation knob 25 is in operation, a wire that is inserted into the insertion section 16 is pushed and pulled so that the bending portion 16b is in bending operation upward, downward, to the left, and to the right. In this manner, the tip portion 16a is directed as desired in the body of the patient.

Figure 2:
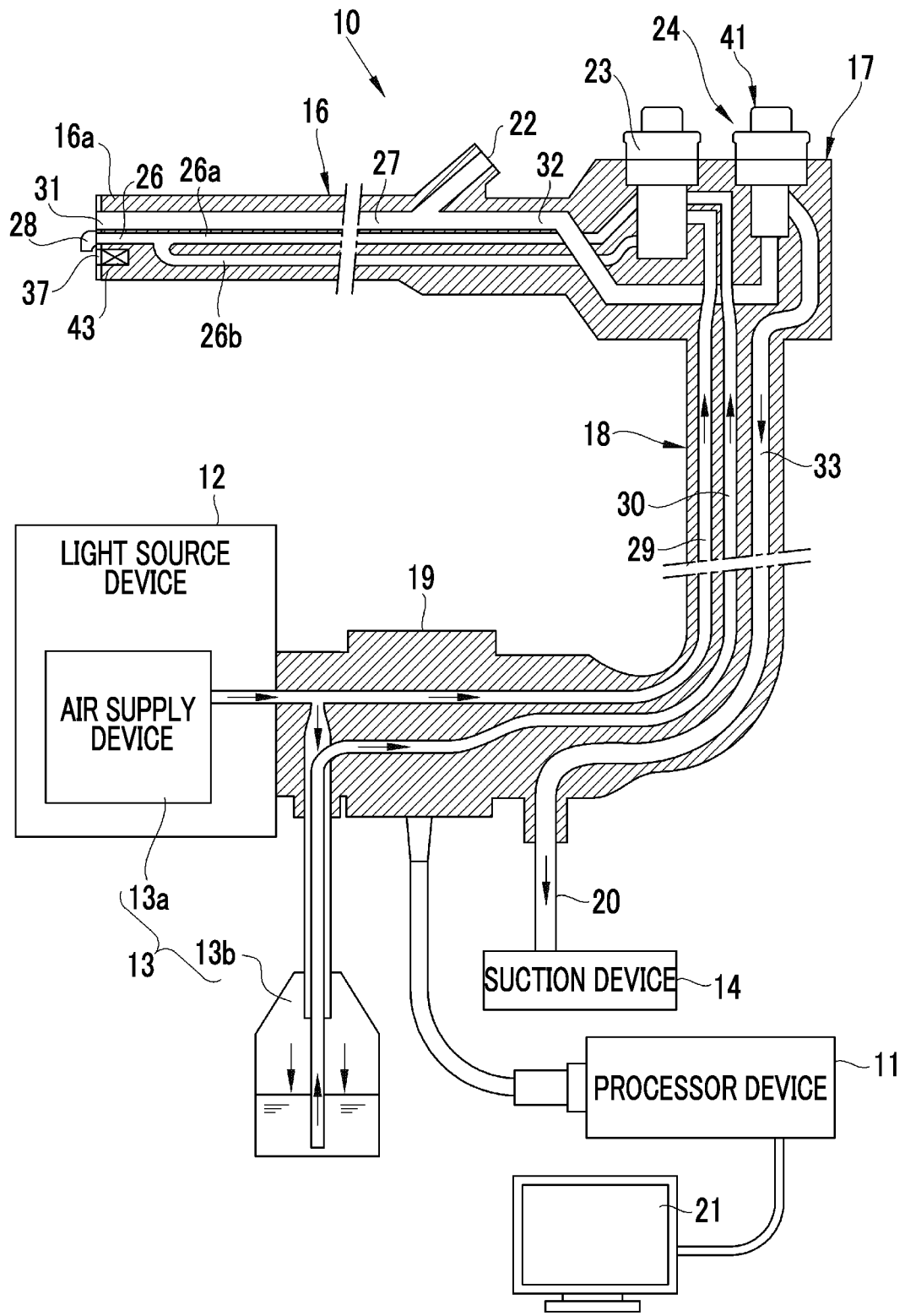
FIG. 2 is a conduit diagram of an electronic endoscope.

As illustrated in FIG. 2, an air/water supply channel 26 and a treatment tool insertion channel 27 are arranged in the insertion section 16 and the hand operation unit 17. One end of the air/water supply channel 26 communicates with an air/water supply nozzle 28 that is disposed in the tip portion 16a. The other end of the air/water supply channel 26 branches into an air supply conduit 26a and a water supply conduit 26b. The air supply conduit 26a and the water supply conduit 26b are connected to the air/water supply button 23 that is disposed in the hand operation unit 17.

Not only the air supply conduit 26a and the water supply conduit 26b but also one end of an air supply source conduit 29 leading to the air supply device 13a and one end of a water supply source conduit 30 leading to the wash water tank 13b are connected to the air/water supply button 23. The air supply device 13a supplies gas (air and carbonic acid gas) during an inspection by the electronic endoscope 10.

When an air supply operation is performed by the air/water supply button 23, the gas that is generated by the air supply device 13a is sent to the air/water supply nozzle 28. When a water supply operation is performed, the wash water is sent to the air/water supply nozzle 28 from the wash water tank 13b due to pressure of the gas that is generated by the air supply device 13a. The air/water supply nozzle 28 washes an observation window 37 by selectively injecting the gas and the wash water that are supplied via the air/water supply channel 26.

One end of the treatment tool insertion channel 27 communicates with a treatment tool outlet (suction port) 31. The other end of the treatment tool insertion channel 27 communicates with the treatment tool inlet 22. Various types of treatment tools where an injection needle, a high-frequency knife, and the like are arranged at tips are inserted into the treatment tool inlet 22, and the treatment tool inlet 22 is closed by a plug (not illustrated) when no treatment tool is inserted. A suction conduit 32 branches from the treatment tool insertion channel 27. The suction conduit 32 is connected to the suction button 24.

Not only a suction tube 38 that has the suction conduit 32 but also a suction source tube 39 (refer to FIG. 5) that has a suction source conduit 33 are connected to the suction button 24. The suction device 14 is provided with a suction pump as a suction source and the like, and remains in operation during the inspection by the electronic endoscope 10. When a suction operation is performed by the suction button 24, suctioning is performed by a negative pressure that is generated by the suction device 14. When a blocking operation is performed, the negative pressure is blocked and the suctioning is stopped.

The suction button 24 is provided with an operation cap 41, and allows the suction source conduit 33 in the suction source tube 39 to communicate with an outside atmosphere in a state where the operation cap 41 is not in operation. This is because the suction device 14 remains in operation and a load on the suction device 14 increases unless the suction source conduit 33 communicates with the outside atmosphere.

When the operation cap 41 is in full-press operation, the suction button 24 allows the suction source conduit 33 to communicate with the suction conduit 32 in the suction tube 38. Then, negative pressure suctioning forces of the suction conduit 32 and the treatment tool insertion channel 27 increase and various types of suctioning objects are suctioned from the treatment tool outlet 31.

Figure 3:
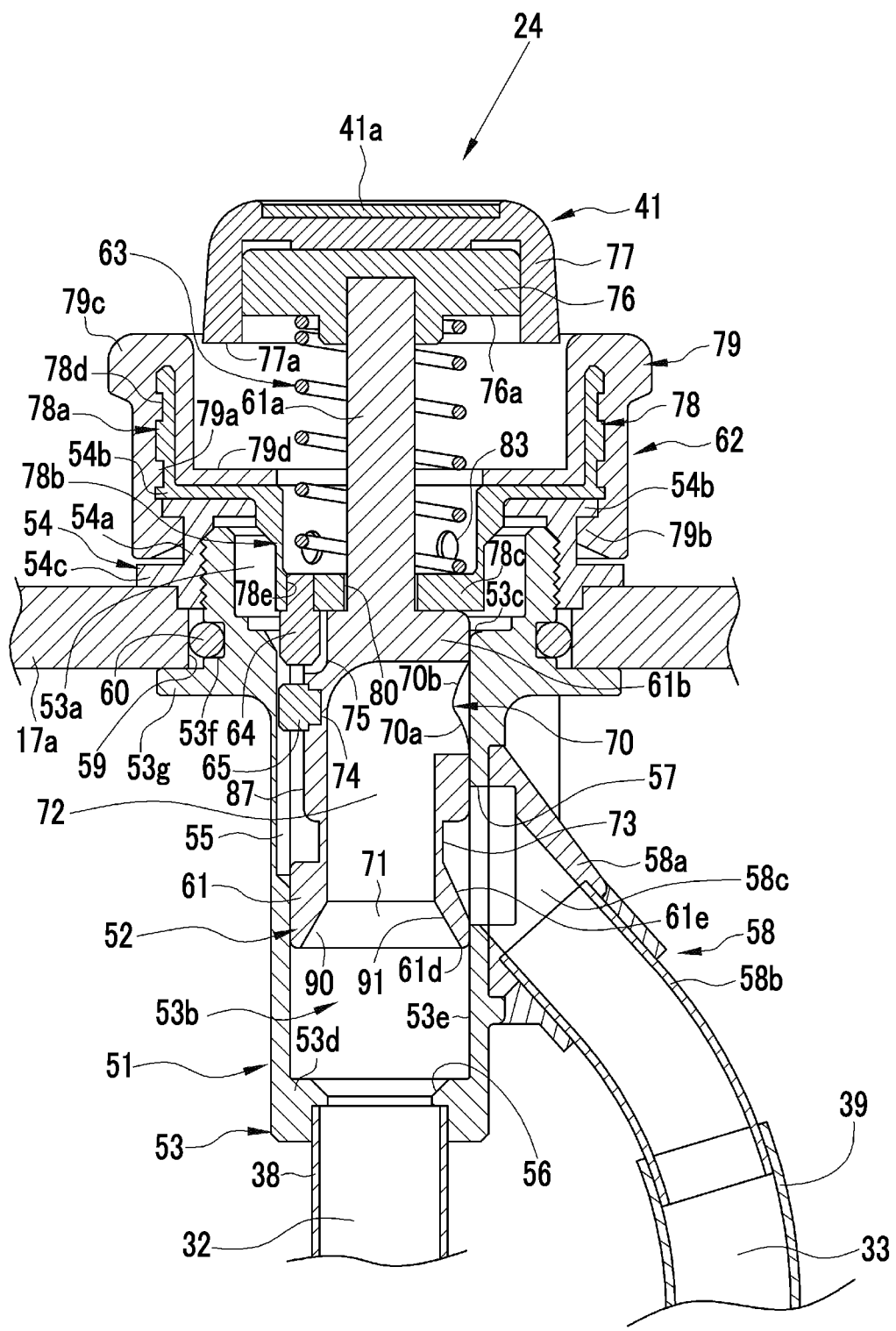
FIG. 3 is a cross-sectional view illustrating a suction button in a non-contact state where an operation cap is not in pressing operation.
Figure 4:
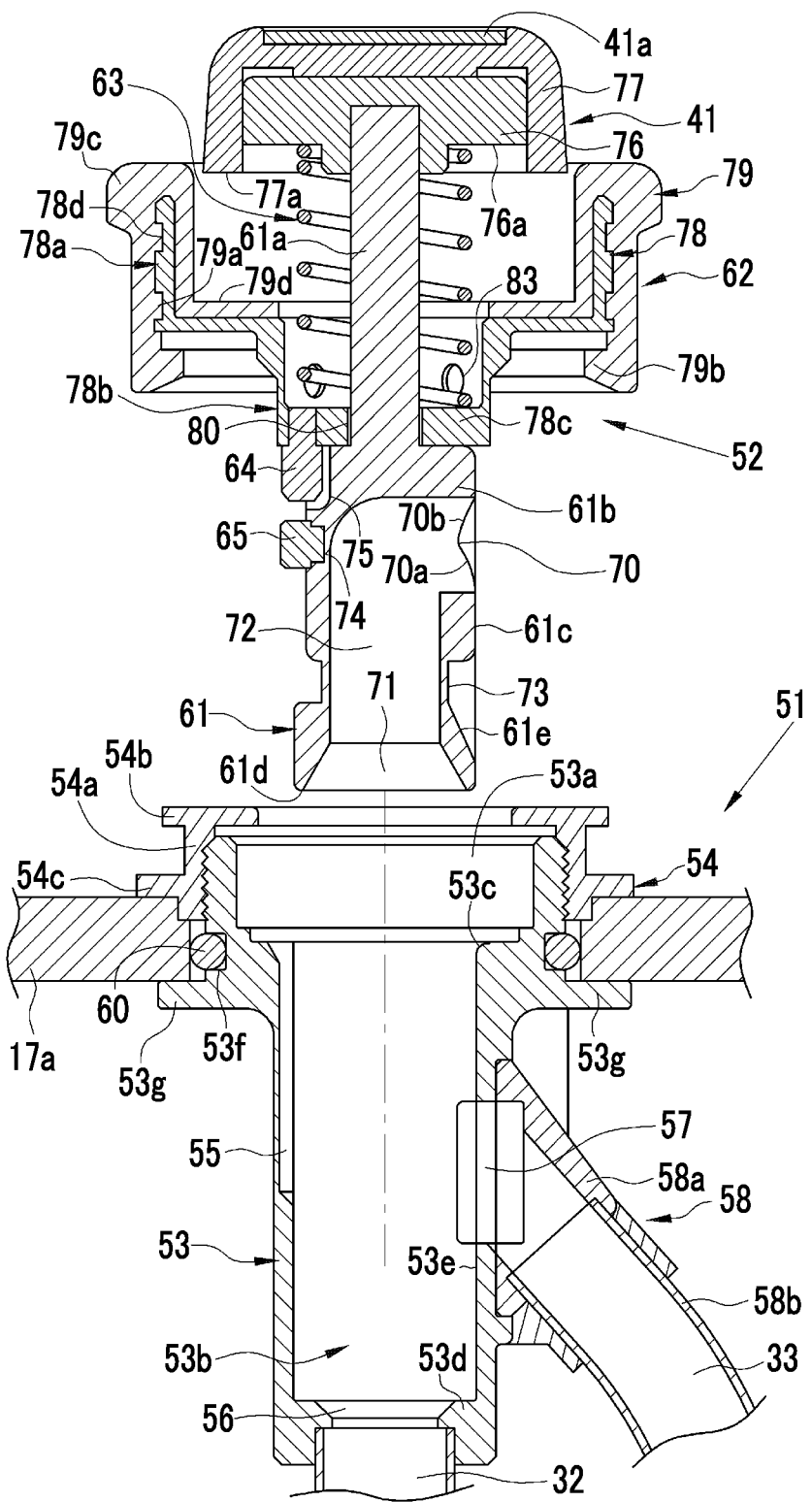
FIG. 4 is a cross-sectional view illustrating a state where a piston unit is removed from a cylinder unit.

As illustrated in FIGS. 3 and 4, the suction button 24 is provided with a cylinder unit 51 and a piston unit 52, and the piston unit 52 is detachably mounted on the cylinder unit 51. In the following description, an upper side end of each of the components in FIGS. 3 and 4 will be referred to as "one end", an upper side end portion of each of the components in FIGS. 3 and 4 will be referred to as "one end portion", a lower side end of each of the components in FIGS. 3 and 4 will be referred to as "the other end", and a lower side end portion of each of the components in FIGS. 3 and 4 will be referred to as "the other end portion".

The cylinder unit 51 has a cylinder 53 and a cap mounting ring 54. A metallic bottomed cylindrical body is an example of what constitutes the cylinder 53. A cylinder cap insertion hole 53a and a piston passage 53b are formed, along a cylinder axis and from the one end toward the other end, in the cylinder 53.

Figure 5:
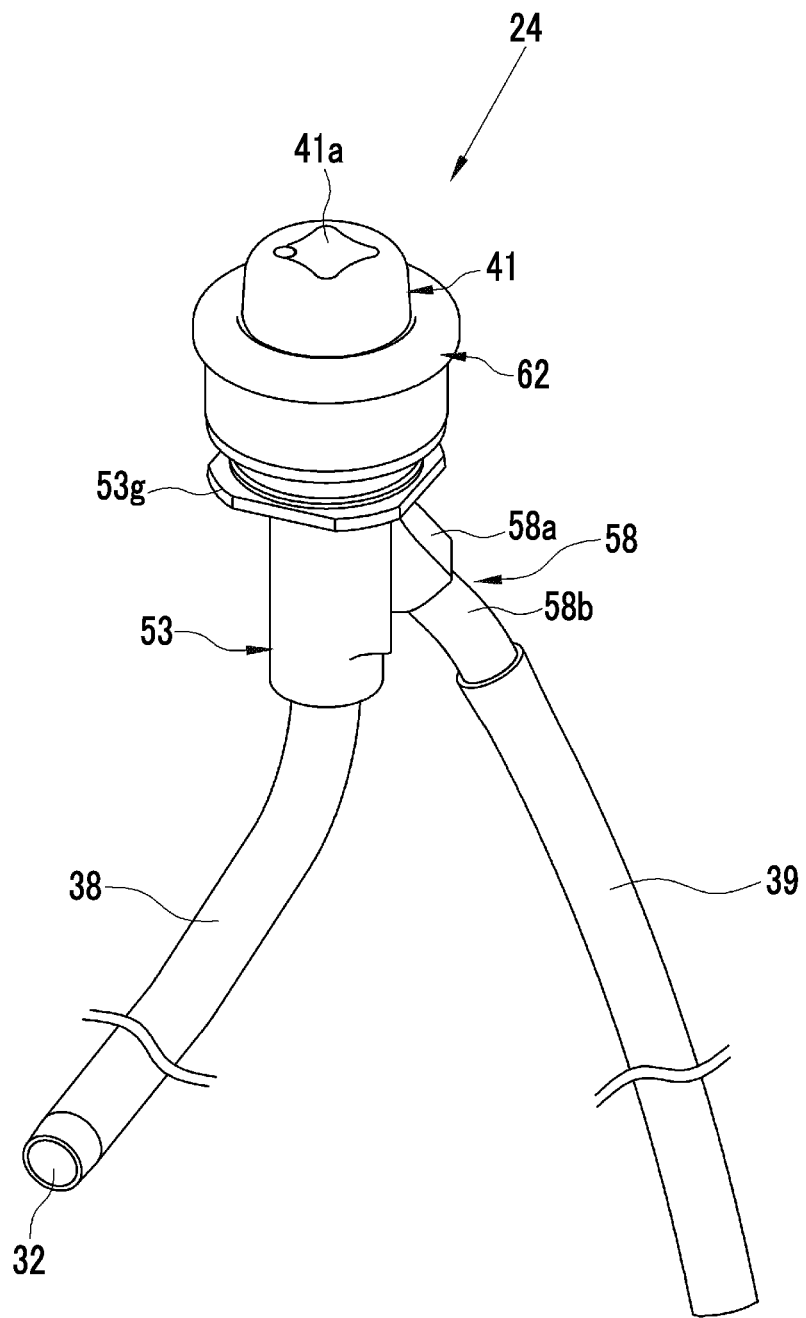
FIG. 5 is a perspective view illustrating the suction button.

The one end of the piston passage 53b is open as a piston insertion port 53c. A suction connection port 56 is formed in a bottom portion 53d that is positioned at the other end of the piston passage 53b. The suction conduit 32 is connected to the suction connection port 56. A suction source connection port 57 is formed in an inner peripheral surface 53e of the piston passage 53b. The suction source conduit 33 is connected to the suction source connection port 57 via a connection portion 58. In the development view illustrated in FIGS. 8A to 8B, the suction source connection port 57 has a rectangular shape with R-shaped corner portions. As illustrated in FIGS. 3 and 5, the connection portion 58 is provided with a fixed portion 58a that is fixed to the cylinder 53 and a connect pipe 58b that is fitted into and fixed to the fixed portion 58a and the suction source tube 39. An inner portion of the connect pipe 58b is the suction source conduit 33 and an inner portion of the fixed portion 58a is a suction source connection passage 58c.

As illustrated in FIGS. 3 and 4, a male screw portion (not illustrated), a circumferential groove 53f, and a mounting flange 53g are formed, in order from above, in an outer peripheral surface of the one end portion of the cylinder 53. A female screw portion (not illustrated) that is formed in an inner peripheral surface of the cap mounting ring 54 is screwed with the male screw portion. The mounting flange 53g abuts against a case 17a of the hand operation unit 17. A cylinder mounting hole 59 is formed in the case 17a for the cylinder 53 to be inserted from below.

A rotation regulating groove 55 is formed in the piston passage 53b. The rotation regulating groove 55 extends to the one end with a part of the inner peripheral surface 53e cut in a cylinder axis direction at a position facing the suction source connection port 57. The rotation regulating groove 55 is used to regulate rotation of a piston 61.

The cap mounting ring 54 has a ring main body 54a having a tubular shape, a cap mounting flange 54b, and a cylinder pressing flange 54c. The cap mounting flange 54b and the cylinder pressing flange 54c are formed, in order from above, on an outer peripheral surface of the ring main body 54a. A female screw portion (not illustrated) is formed in an inner peripheral surface of the ring main body 54a. The female screw portion is formed in the inner peripheral surface of a lower end portion of the ring main body 54a and is screwed with the male screw portion of the cylinder 53. This screwing causes the cylinder pressing flange 54c and the mounting flange 53g to pinch the case 17a in a peripheral portion of the cylinder mounting hole 59, and thus the cylinder 53 is mounted on the case 17a. An O-ring 60 is put into the circumferential groove 53f. The O-ring 60 holds a gap between the case 17a and the cylinder 53 to be watertight.

The piston unit 52 has the piston 61, a cylinder cap 62, the operation cap 41, a coil spring 63, a cap rotation regulation pin 64, and a piston rotation regulation pin 65. The piston 61 has, from above, a piston tip portion 61a and a piston main body 61b and is formed to have a two-stage shaft shape with the piston tip portion 61a smaller in diameter than the piston main body 61b.

Figure 6:
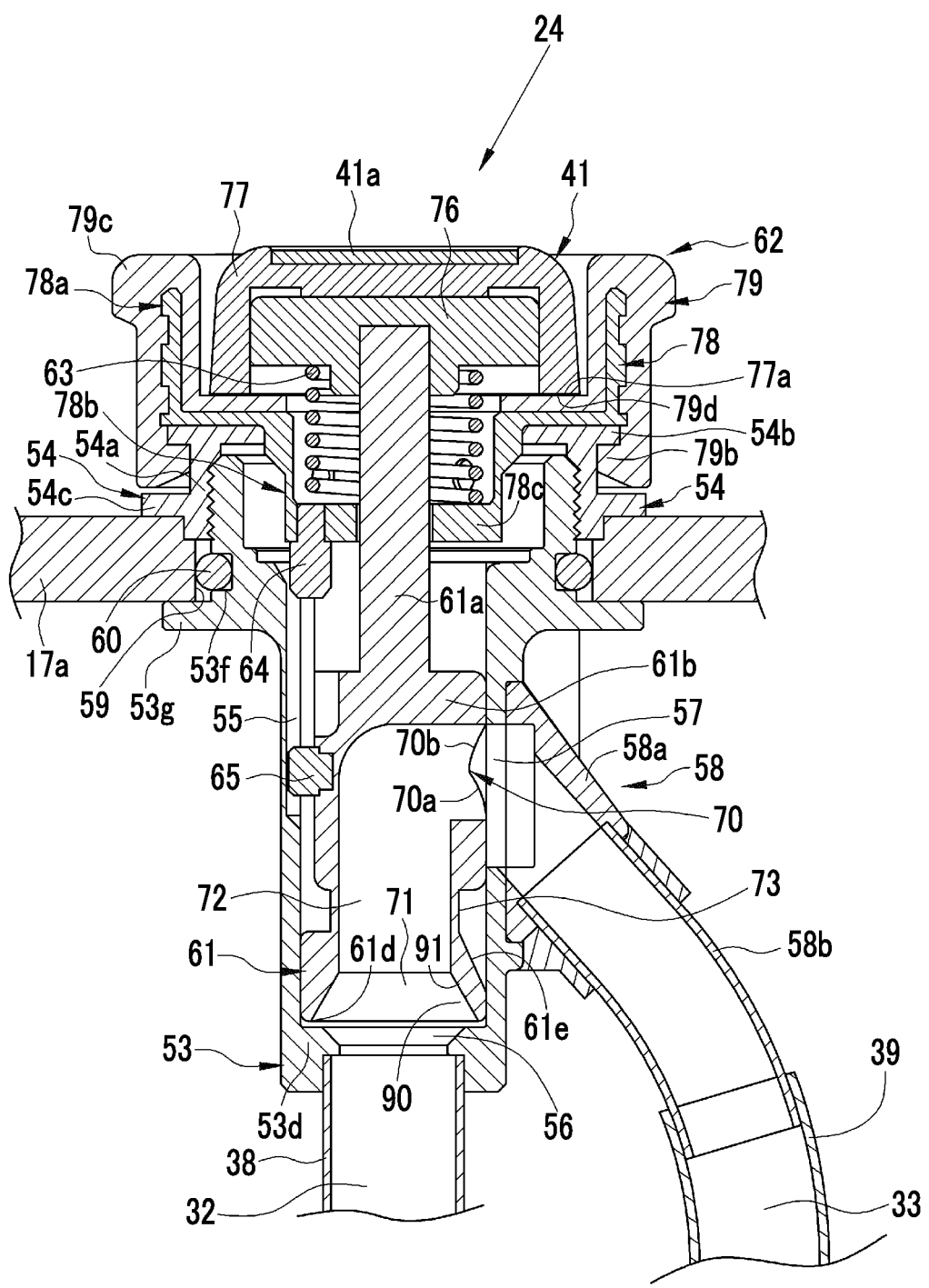
FIG. 6 is a cross-sectional view illustrating the suction button in a suction state where the operation cap is pushed.

An outer peripheral surface opening 70 that is open to an outer peripheral surface 61c, the other end opening 71 that is open to the other end 61d, and an L-shaped first communication passage 72 that allows the openings 70 and 71 to communicate with each other are formed in the piston main body 61b. A circumferential groove 73 is formed in the outer peripheral surface 61c of the piston main body 61b. A regulation pin accommodation groove 75 is formed, on the side opposite to the outer peripheral surface opening 70, in the outer peripheral surface 61c. A mounting hole 74 is formed below the regulation pin accommodation groove 75. The regulation pin accommodation groove 75 is formed from the one end toward the other end and in parallel to the cylinder axis. An inclined notch 61e that continues from the circumferential groove 73 is formed, on the other end side from the circumferential groove 73 and at the same circumferential-direction position as the outer peripheral surface opening 70, in the outer peripheral surface 61c. The inclined notch 61e communicates with the suction source connection port 57 when the piston 61 is positioned at the first position that is illustrated in FIG. 3. The inclined notch 61e faces the inner peripheral surface 53e of the piston passage 53b when the piston 61 is positioned at the second position that is illustrated in FIG. 6. The inclined notch 61e is formed in a direction in which the suction source connection passage 58c extends in the fixed portion 58a.

The outer peripheral surface opening 70 faces the inner peripheral surface 53e of the piston passage 53b when the piston 61 is positioned at the first position. The outer peripheral surface opening 70 is formed at a position facing the suction source connection port 57 when the piston 61 is positioned at the second position. The outer peripheral surface opening 70 is smaller than the suction source connection port 57.

Figure 7:
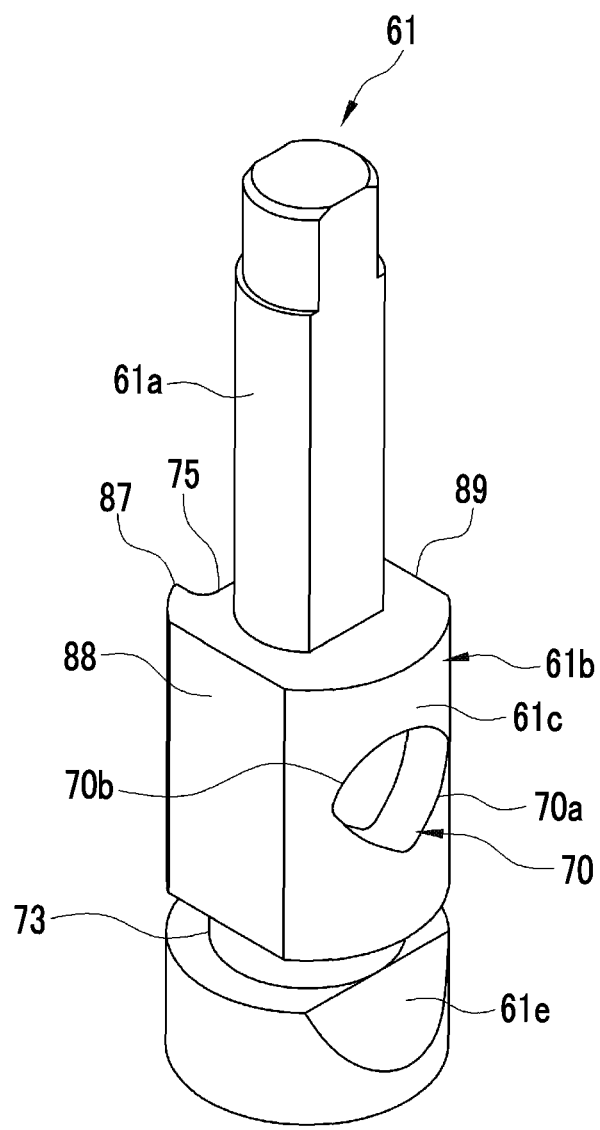
FIG. 7 is a perspective view illustrating a piston.

As illustrated in FIGS. 3 and 7, the outer peripheral surface opening 70 is provided with a V-shaped opening portion 70a and an arc-shaped opening portion 70b. When the piston 61 is moved from the first position to the second position, the V-shaped opening portion 70a, which is a correction opening portion, allows an increment of a communication opening width at which the suction source connection port 57 and the outer peripheral surface opening 70 overlap with each other to be three times or less an increment of a pressing stroke of the piston 61. Accordingly, the V-shaped opening portion 70a is formed to have a V shape as illustrated in the development view of FIGS. 8A to 8D and is formed at a part where the suction source connection port 57 and the outer peripheral surface opening 70 start overlapping. In this embodiment, a V angle θ of the V-shaped opening portion 70a is equal to 90°, and the increment of the communication opening width is approximately double the increment of the pressing stroke of the piston 61. The arc-shaped opening portion 70b continues from the V-shaped opening portion 70a and is formed to have an arc shape. When the piston 61 is moved from the first position to the second position, the V-shaped opening portion 70a first communicates with the suction source connection port 57. The angle of the V-shaped opening portion 70a and an arc size of the arc-shaped opening portion 70b can be appropriately changed. The V shape includes those with the tip portion having an R shape and with the tip portion having an angular shape. The increment of the communication opening width may be equal to or more than 1.0 times and equal to or less than 3.0 times the increment of the pressing stroke of the piston 61. Preferably, the increment of the communication opening width is equal to or more than 1.0 times and equal to or less than 2.5 times the increment of the pressing stroke of the piston 61. In a case where the increment of the communication opening width is less than 1.0 times the increment of the pressing stroke of the piston 61, the increment is insufficient, a suction amount is insufficient, and the suctioning object, particularly filth, is likely to cause clogging. In a case where the increment of the communication opening width exceeds 3.0 times the increment of the pressing stroke of the piston 61, the increment is excessive and the suction amount rapidly increases.

The operation cap 41 is fixed to the one end of the piston tip portion 61a. The operation cap 41 has a metallic cap main body 76 and a resinous cover 77 that covers the one end surface and an outer peripheral surface of the cap main body 76. An index 41a is disposed on an upper surface of the cover 77. The index 41a shows a pressing position for a pressing operation.

The cylinder cap 62 and the coil spring 63 are arranged between the operation cap 41 and the piston main body 61b in a state where the piston tip portion 61a is inserted. A metallic, stepped, and bottomed tubular body 78 that has an upper tubular section 78a and a lower tubular section 78 and a cover 79 constitute the cylinder cap 62. A tip portion insertion hole 80 is formed in a bottom portion 78c of the lower tubular section 78b. The piston tip portion 61a is inserted into the tip portion insertion hole 80. A plurality of ventilation holes 83 are formed in the lower tubular section 78b. The ventilation holes 83 lead to the outside atmosphere.

The cover 79 is made of rubber or resin and is fitted onto the upper tubular section 78a. A locking groove 78d is formed in an outer peripheral surface of the upper tubular section 78a, and a locking ridge 79a that is fitted into the locking groove 78d is formed in the cover 79. Since the locking ridge 79a is fitted into the locking groove 78d, the cover 79 is held not to fall off the upper tubular section 78a. The cover 79 is formed to have a bottomed tubular shape and covers the outer peripheral surface and an inner peripheral surface of the upper tubular section 78a.

A locking claw 79 is formed to protrude toward an inner side of an inner peripheral surface of a lower end portion of the cover 79. The locking claw 79b is locked to the cap mounting flange 54b over the cap mounting flange 54b when the piston unit 52 is mounted on the cylinder unit 51 (refer to FIG. 3). In this manner, the piston unit 52 can be reliably mounted on the cylinder unit 51 as illustrated in FIG. 3. For removal, the piston unit 52 is lifted with an upper flange 79c of the cylinder cap 62 held. In this manner, the locking between the locking claw 79b and the cap mounting flange 54b is released.

After the electronic endoscope 10 is used, the suction conduit 32, the suction source conduit 33, the piston passage 53b, and the like are dirty due to the suctioning object such as a liquid, and thus should be carefully washed by using a cleaning brush or the like. When the locking between the locking claw 79b and the cap mounting flange 54b is released and the piston unit 52 is removed from the cylinder unit 51 as illustrated in FIG. 4, the suction conduit 32, the suction source conduit 33, and the piston passage 53 are exposed from the piston insertion port 53c and can be washed with ease. The piston unit 52 is discarded after the piston unit 52 is used and is replaced with a new piston unit. Alternatively, the piston unit 52 is re-used after being washed.

As illustrated in FIG. 3, the coil spring 63 is compressed in a state where the one end abuts against the other end surface 76a of the cap main body 76 and the other end abuts against the bottom portion 78c of the lower tubular section 78. Accordingly, the operation cap 41 remains in a state of being biased toward the one end side in the cylinder cap 62 by the coil spring 63. The one end of the piston main body 61 abuts against the bottom portion 78c that is the other end surface of the cylinder cap 62.

The bottom portion 78c is formed for a pin mounting hole 78e to be parallel to a center line of the cylinder 53. The one end portion of the cap rotation regulation pin 64 is fixed to the pin mounting hole 78e. The cap rotation regulation pin 64 protrudes from a bottom surface of the bottom portion 78c and is accommodated in the regulation pin accommodation groove 75 of the piston main body 61b. The cap rotation regulation pin 64 is accommodated in the regulation pin accommodation groove 75, and thus a relative rotation between the piston 61 and the cylinder cap 62 is regulated.

The piston rotation regulation pin 65 is attached to the mounting hole 74 of the piston 61. The piston rotation regulation pin 65 and the rotation regulating groove 55 of the cylinder 53 function as rotation regulating units for the cylinder 53 and the piston 61. The piston rotation regulation pin 65 is put into and locked by the rotation regulating groove 55 and regulates a relative rotation between the cylinder 53 and the piston 61.

An inner diameter of the tip portion insertion hole 80 of the cylinder cap 62 into which the piston tip portion 61a is inserted is larger than an outer diameter of the piston tip portion 61a and is smaller than an outer diameter of the piston main body 61, and thus the bottom portion 78c abuts against the one end of the piston main body 61. Accordingly, separation of the piston 61 from the cylinder 53 via the cylinder cap 62 and the cap mounting ring 54 is regulated.

The piston 61 is positioned by the cylinder cap 62 and is displaced between the first position that is illustrated in FIG. 3 and the second position that is illustrated in FIG. 6. At the first position, the operation cap 41 is not in operation and is in a non-contact state with the operation cap 41 is farthest from the piston insertion port 53c. When the operation cap 41 is in the non-contact state, the piston 61 is biased to the one end side of the cylinder 53 via the operation cap 41 by the coil spring 63, abuts against the bottom portion 78c, and is stationary. The piston 61 is at the first position in this manner. At the second position, the operation cap 41 is in a pushed state due to the pressing operation and the operation cap 41 is closest to the piston insertion port 53c with an additional push being regulated. In a state where the operation cap 41 is pushed, the piston 61 is moved to the other end side of the cylinder 53 against the biasing by the coil spring 63. As a result, the operation cap 41 is accommodated in the cylinder cap 62, and a bottom surface 77a of the cover 77 abuts against an inner bottom surface 79d of the cover 79 and is stationary. In this manner, the piston 61 is positioned at the second position.

At the first position, the circumferential groove 73 is positioned in the suction source connection port 57. The circumferential groove 73 is formed over an entire circumference of the piston main body 61b. Three notch passages 87, 88, and 89 (refer to FIG. 7) are formed, at 90° intervals in a circumferential direction from the circumferential groove 73 to the one end of the piston main body 61, in the outer peripheral surface 61c of the piston main body 61 to communicate with the circumferential groove 73. The notch passages 87 to 89 are formed by cutting the outer peripheral surface of the piston into a planar shape. Accordingly, a second communication passage that has the circumferential groove 73 and the notch passages 87 to 89 allows the suction source connection port 57 to communicate with the outside atmosphere via the circumferential groove 73, the notch passages 87 to 89, an inner space of the cap mounting ring 54, and the ventilation holes 83 when the piston 61 is at the first position, and thus the suction device 14 suctions from the outside atmosphere. The circumferential groove 73 does not necessarily have to be formed over the entire circumference of the piston main body 61b. The circumferential groove 73 may be formed at a circumferential-direction part of the piston main body 61 insofar as communication with the suction source connection port 57 and communication with the notch passages 87 to 89 are ensured at the first position.

When the piston 61 is at the first position, the inclined notch 61e forms a straight line with the suction source connection passage 58c in the fixed portion 58a and communication with the outside atmosphere is performed without resistance.

As illustrated in FIG. 6, the outer peripheral surface opening 70 is positioned in the suction source connection port 57 at the second position. The first communication passage 72 that allows the outer peripheral surface opening 70 and the other end opening 71 to communicate with each other is formed in the piston 61, and thus the suction device 14 suctions from the suction conduit 32. Accordingly, the suctioning object can be suctioned from the treatment tool outlet 31 in the tip portion 16a.

At the second position, the other end 61d of the piston 61 that has the other end opening 71 approaches or abuts against the bottom portion 53d of the piston passage 53b. If the suctioning object stays between the other end 61d of the piston 61 and the bottom portion 53d of the piston passage 53b, adhesion increases with time and a return operation of the piston 61 may be hindered. This tendency is particularly conspicuous in a case where the suctioning object is a contrast agent.

The contrast agent is used for observation purposes to highlight a specific tissue in a living body such as a blood vessel and add contrast to an image. In this case, a fluorescent image is observed through contrast agent administration to an affected part and irradiation with excitation light having a specific wavelength. The contrast agent is also used during X-ray imaging of the affected part. In this case, the contrast agent is injected into the affected part by taking a cannula or the like out of the treatment tool outlet 31 and the part is imaged by a fluoroscopic apparatus.

Accordingly, a residue relief section 90 is disposed in the other end opening 71. A taper 91 constitutes the residue relief section 90 and an opening cross-sectional area of the residue relief section 90 gradually increases toward the other end 61d. It is preferable that the taper 91 be formed to have a maximum diameter that is equal to an outer diameter of the outer peripheral surface 61c. This includes a case where the maximum diameter of the taper 91 is slightly smaller than the outer diameter of the outer peripheral surface 61c.

When the piston 61 is at the second position, the taper 91 allows the contrast agent that adheres between the other end 61d of the piston 61 and the bottom portion 53d of the piston passage 53b which face each other to be suctioned with ease. In this manner, the contrast agent is discharged from the first communication passage 72 to the suction source conduit 33. A facing area between the other end 61d of the piston 61 and the bottom portion 53d is decreased by the taper 91, and thus the contrast agent that adheres between the cylinder 53 and the piston 61 is decreased and adhesion between the piston 61 and the cylinder 53 can be prevented.

Hereinafter, an effect of the electronic endoscope 10 that has the above-described configuration, particularly an effect of the suction button 24, will be described in detail. After preparation of the inspection by the endoscope system 2 is completed, the camera unit 43 is operated and air supply by the air supply device 13a and suctioning by the suction device 14 continue being performed. After the completion of the preparation, the insertion section 16 is inserted into the body, for example, into a digestive tract. Light from the light source device 12 is emitted into the digestive tract through the universal cord 18, an optical fiber cable in the insertion section 16, and an illumination window (not illustrated) of the tip portion 16a. The camera unit 43 in the tip portion 16a internally images the digestive tract and outputs the imaging signal. The imaging signal is input into the processor device 11 via the transmission cable in the insertion section 16 and the universal cord 18 and is displayed on the monitor 21.

During digestive tract observation, the air/water supply button 23 is operated if an observation object or the observation window 37 of the tip portion 16a needs to be washed or the like. After the air supply operation is performed by the air/water supply button 23, the gas that is generated by the air supply device 13a is sent to the air/water supply nozzle 28. After the water supply operation is performed, the wash water is sent to the air/water supply nozzle 28 from the wash water tank 13 due to the pressure of the gas that is generated by the air supply device 13a. The air/water supply nozzle 28 selectively injects the gas and the wash water supplied via the air/water supply channel 26.

In a case where the affected part is found during the observation of the digestive tract, the treatment tool that is suitable for treatment of the affected part is inserted into the treatment tool inlet 22 of the electronic endoscope 10 and is allowed to protrude from the treatment tool outlet 31 so that the affected part is treated.

In a case where the suctioning from the treatment tool outlet 31 is not performed during the observation of the digestive tract, the operation cap 41 is in the non-contact state and the piston 61 is at the first position in the suction button 24 as illustrated in FIG. 3. In a state where the piston 61 is at the first position, the circumferential groove 73 communicates with the suction source connection port 57. However, the outer peripheral surface opening 70 does not communicate with the suction source connection port 57 and is closed while facing the inner peripheral surface 53e of the piston passage 53b.

In a state where the piston 61 is at the first position, the suction source connection port 57 communicates with the outside atmosphere via the circumferential groove 73, a gap between the notch passages 87 to 89 and the piston passage 53b, the inner space of the cap mounting ring 54, the ventilation holes 83, an inner space of the bottomed tubular body 78, and a gap between the cover 77 and the cover 79. As a result, the load on the suction device 14 can be prevented even when the suctioning from the treatment tool outlet 31 is not performed.

Figure 8A:
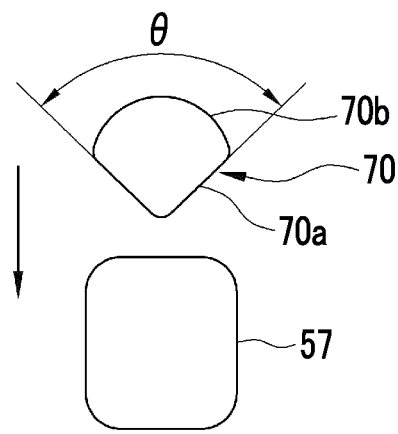
FIG. 8A is a development view illustrating an outer peripheral surface opening of the piston and a suction source connection port of a cylinder at a time when the piston is positioned at a first position.
Figure 8B:
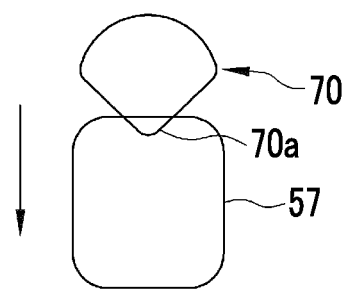
FIG. 8B is a development view illustrating a state where a part of a V-shaped opening portion of the outer peripheral surface opening communicates with the suction source connection port.

In a case where the suctioning object such as blood and the filth in the body is suctioned during the observation of the digestive tract, the operation cap 41 is pressed and the piston 61 is moved from the first position toward the second position. In this case, the outer peripheral surface opening 70 of the piston 61 and the suction source connection port 57 are changed from the state that is illustrated in FIG. 8A and the V-shaped opening portion 70a of the outer peripheral surface opening 70 first communicates with the suction source connection port 57 as illustrated in FIG. 8B. Since the outer peripheral surface opening 70 and the suction source connection port 57 communicate with each other, the suction source conduit 33 and the suction conduit 32 communicate with each other via the suction source connection passage 58c, the suction source connection port 57, the outer peripheral surface opening 70, the first communication passage 72, the other end opening 71, and the suction connection port 56.

Figure 8C:
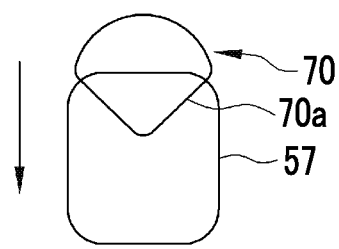
FIG. 8C is a development view illustrating a state where the V-shaped opening portion of the outer peripheral surface opening communicates with the suction source connection port.
Figure 8D:
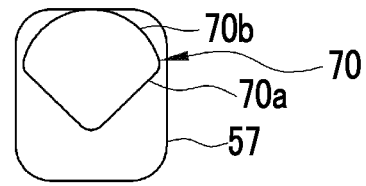
FIG. 8D is a development view illustrating a state where the V-shaped opening portion and an arc-shaped opening portion of the outer peripheral surface opening communicate with the suction source connection port.

When the piston 61 is further pressed as illustrated in FIG. 8C, the entire V-shaped opening portion 70a communicates with the suction source connection port 57. Then, the arc-shaped opening portion 70b also communicates with the suction source connection port 57 after the piston 61 is moved to the second position as illustrated in FIG. 8D. Since the outer peripheral surface opening 70 is smaller than the suction source connection port 57, the V-shaped opening portion 70a and the arc-shaped opening portion 70 reliably communicate with the suction source connection port 57.

When the suction source conduit 33 and the suction conduit 32 communicate with each other, various types of the suctioning objects are suctioned from the treatment tool outlet 31. The suctioning objects are suctioned to the suction device 14 via the treatment tool insertion channel 27, the suction conduit 32, the suction connection port 56, the other end opening 71, the first communication passage 72, the outer peripheral surface opening 70, the suction source connection port 57, the suction source connection passage 58c, and the suction source conduit 33.

In this embodiment, the taper 91 as the residue relief section 90 is disposed in the other end opening 71 of the piston 61, and thus the adhesion between the piston 61 and the cylinder 53 can be prevented during the endoscopic inspection using the contrast agent. Accordingly, the pressing operation by the suction button 24 can be smoothly performed over a long period of time and operability can be improved.

In a case where the suctioning is stopped, the pressing of the operation cap 41 is released. Then, the piston 61 returns to the first position that is illustrated in FIG. 3 due to a biasing force of the coil spring 63. Then, the insertion section 16 is pulled out of the digestive tract after the termination of the digestive tract observation.

Figure 9:
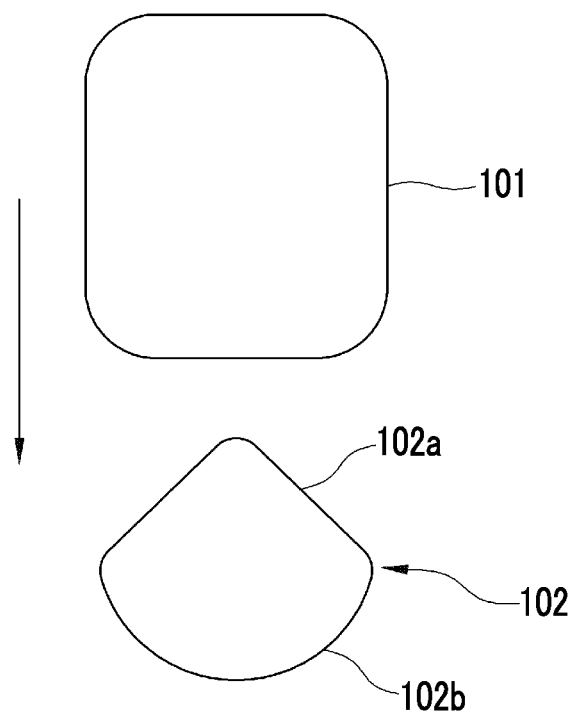
FIG. 9 is an explanatory drawing of an embodiment in which the outer peripheral surface opening has a rectangular shape and the suction source connection port is shaped to have the V-shaped opening portion and the arc-shaped opening portion.

In the embodiment described above, the outer peripheral surface opening 70 of the piston 61 is shaped to have the V-shaped opening portion 70a (correction opening portion) and the arc-shaped opening portion 70b and the suction source connection port 57 of the cylinder 53 has a rectangular shape. However, as illustrated in FIG. 9, an outer peripheral surface opening 101 may have a rectangular shape and a suction source connection port 102 may be shaped to have a V-shaped opening portion 102a and an arc-shaped opening portion 102b.

In the embodiments described above, the outer peripheral surface opening 70 and the suction source connection port 102 are shaped to have the V-shaped opening portions 70a and 102a and the arc-shaped opening portions 70b and 102b. However, formation of a triangular shape with no arc-shaped opening portion is also possible. In addition, the V-shaped opening portion as the correction opening portion may be formed at a part of the opening and may not be in right-left symmetry.

In a case where one of the suction source connection port and the outer peripheral surface opening is circular, oblong, or the like in shape, the shape of the other one is determined so that the increment of the communication opening width at which the suction source connection port and the outer peripheral surface opening overlap with each other is three times or less the increment of the pressing stroke of the piston. In addition, the operability may be improved by determining the shapes of the suction source connection port and the outer peripheral surface opening for the suction amount to increase in a desired rise curve instead of the suction amount linearly increasing with respect to the pressing amount of the piston. For example, the shape of the correction opening portion is not limited to the V shape and may be a bent shape in which each V-shaped side swells to an inner side, a bent shape in which each V-shaped side swells to an outer side, or another shape. The correction opening portion may be formed in any one of the suction source connection port and the outer peripheral surface opening and may be formed in both of the suction source connection port and the outer peripheral surface opening.

Figure 10:
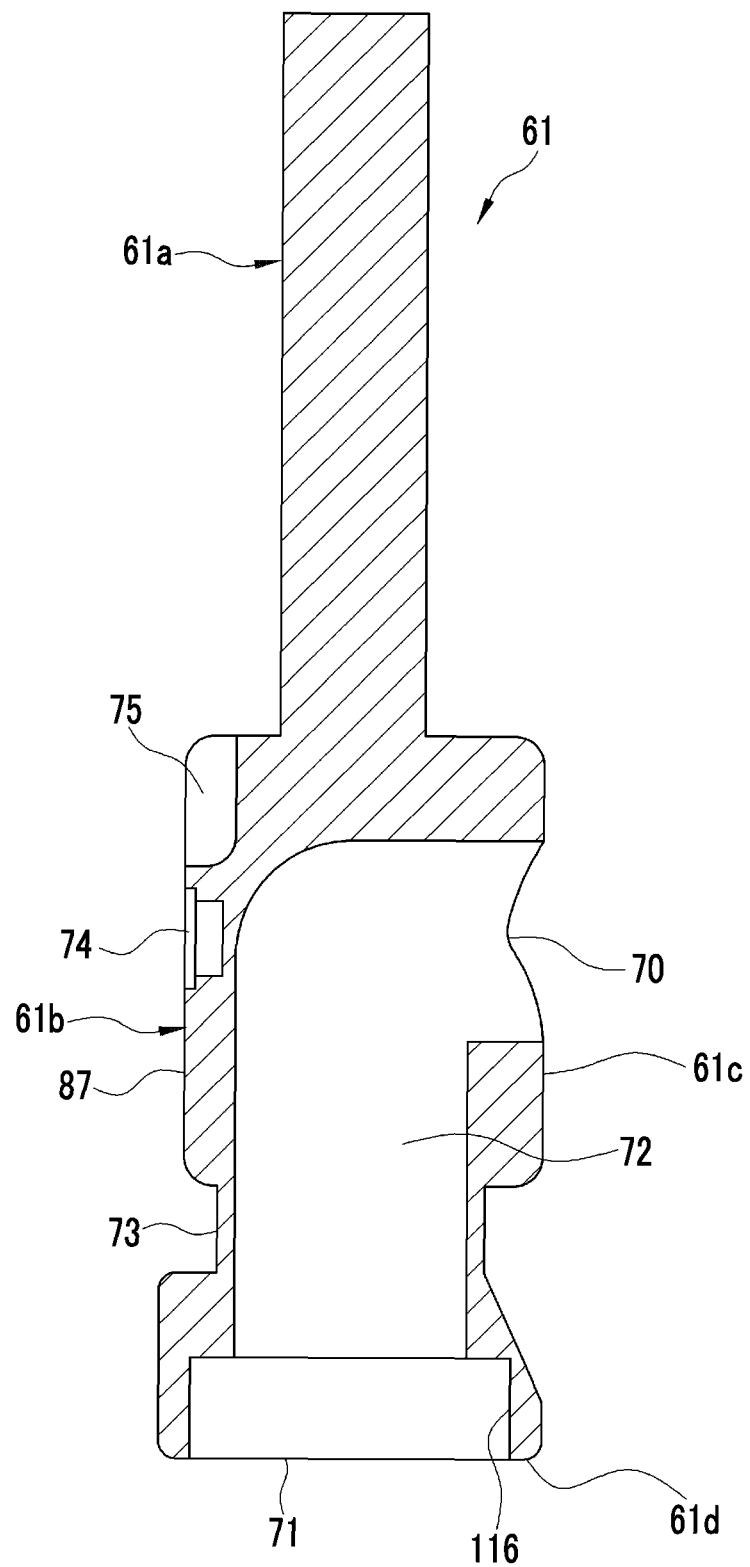
FIG. 10 is a cross-sectional view of a piston of another embodiment in which a step portion is formed at the other end abutting against a cylinder.

In the embodiment described above, an example has been described in which the taper 91 is formed as the residue relief section 90 in the other end opening 71 of the piston 61. However, the claimed invention is not limited thereto. As illustrated in FIG. 10, a step portion 116 in which the other end opening 71 is formed to have an inner diameter that is larger than that of the first communication passage 72 may be formed in the piston 61 as the residue relief section. In this case, the contrast agent that adheres between the cylinder 53 and the piston 61 is decreased and the adhesion between the piston 61 and the cylinder 53 can be prevented.

Figure 11:
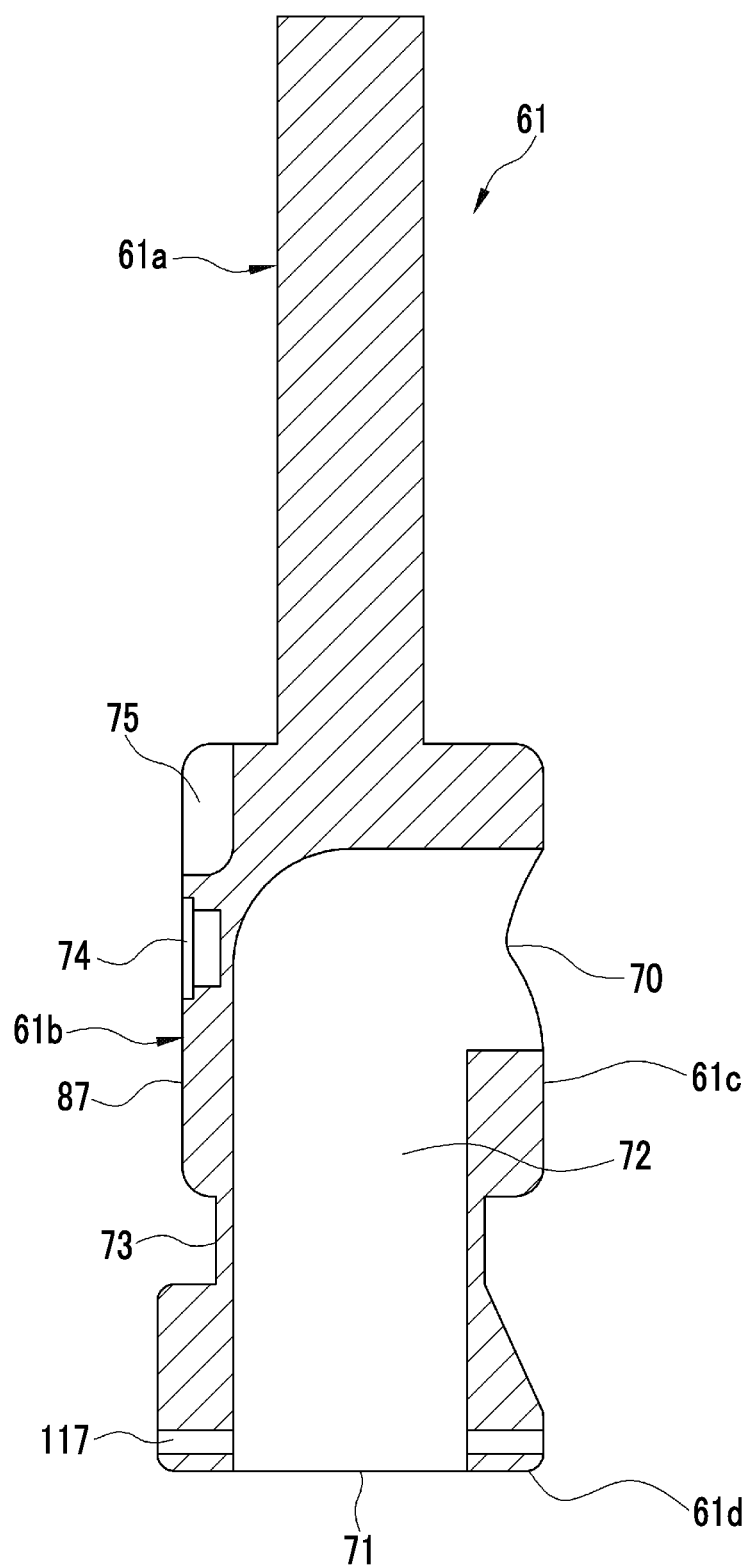
FIG. 11 is a cross-sectional view of a piston of yet another embodiment in which a through-hole is formed at a position continuous to the other end abutting against a cylinder.

As illustrated in FIG. 11, a through-hole 117 that is formed at a position in the piston 61 which is contiguous to the suction connection port 56 and penetrates the outer peripheral surface 61c from the first communication passage 72 may be the residue relief section. In this case, the contrast agent is discharged from the outer peripheral surface side through the through-hole 117 even when the contrast agent is suctioned from the suction tube 38 and is moved into the first communication passage 72, and thus the contrast agent is unlikely to adhere between the cylinder 53 and the piston 61. The above-described configurations may be combined with each other as the residue relief section. For example, the taper and the step portion may be formed in the other end opening 71 with the through-hole being disposed.

In the embodiments described above, examples of the electronic endoscope that is used to observe the image obtained by imaging the state of the affected part of the body or the like with the imaging device have been described. However, the claimed invention is not limited thereto. The claimed invention can also be applied to an endoscope that is used to observe a state of an affected part or the like by adopting an optical image guide.

EXAMPLE

Hereinafter, the claimed invention will be described in detail by using examples. However, contents of the claimed invention are not limited thereto.

In the first example, the electronic endoscope 10 in which the suction button 24 of the claimed invention is incorporated was used in measuring the suction amount at a time when the operation cap 41 is pressed and air is suctioned. An electric portable aspirator (MINIC W-II MW2-1400) manufactured by Sanko Manufacturing Co., Ltd. was used and suctioning was performed at 40 kPa, and the suction amounts at a time when the operation cap 41 is pressed every 0.1 mm by the Outside Micrometer (MDC-100MJ) manufactured by Mitutoyo Corporation were measured by using a flow rate sensor amplifier (FD-V40A) and a flow rate sensor head (FD-A10) manufactured by Keyence Corporation.

In the second example, the piston was mounted with a V angle of the V-shaped opening portion of 60°. In a case where the V angle was 60°, the increment of the communication opening width at which the suction source connection port and the outer peripheral surface opening overlap with each other was 1.15 times the increment of the pressing stroke of the piston when the piston was moved from the first position to the second position. The other conditions were identical to those of the first example.

In the first comparative example, a piston of the related art with a circular outer peripheral surface opening was mounted. The other conditions were identical to those of the first example.

Figure 12:
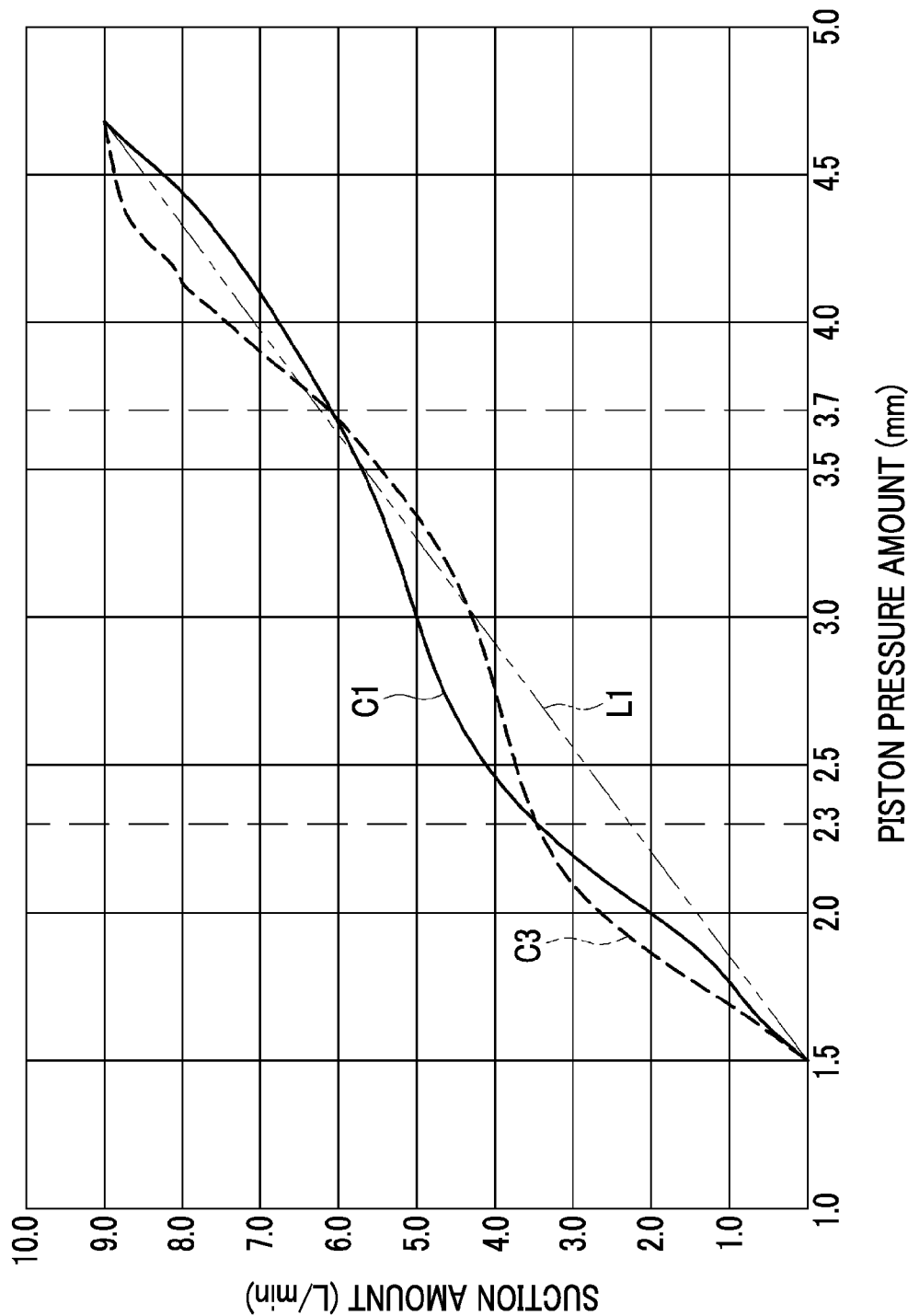
FIG. 12 is a graph illustrating a suction amount with respect to a pressing amount of the piston of the first embodiment.
Figure 13:
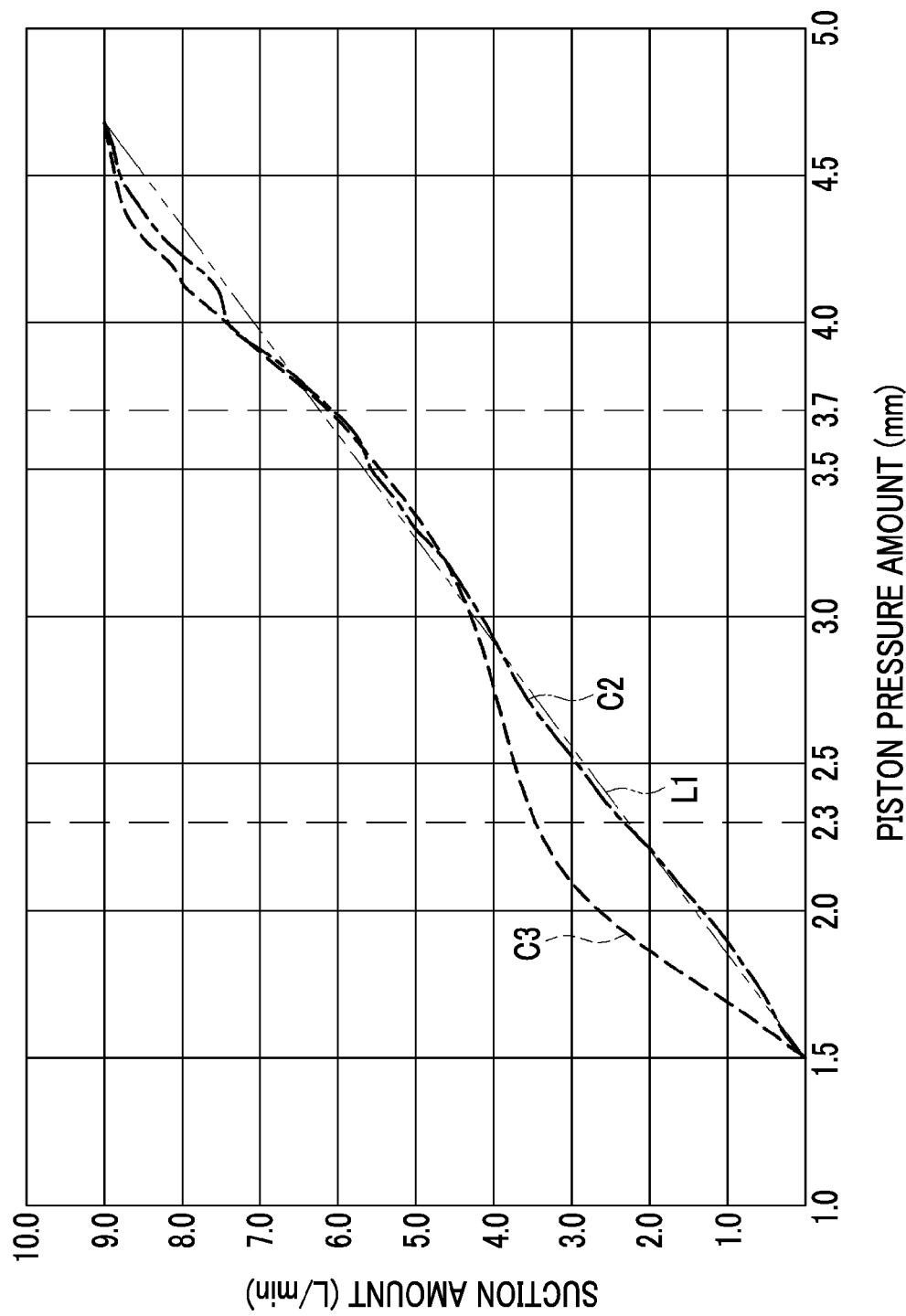
FIG. 13 is a graph illustrating a suction amount with respect to a pressing amount of the piston of the second embodiment.

Test results regarding the first example and the first comparative example are illustrated in FIG. 12, and test results regarding the second example and the second comparative example are illustrated in FIG. 13. FIGS. 12 and 13 illustrate the suction amount (L/min) with respect to the pressing amount. The two-dot chain line L1 represents an ideal line (line in which the suction amount linearly increases with respect to the pressing amount), the solid line C1 represents the first example, the one-dot chain line C2 represents the second example, and the dashed line C3 represents the comparative example.

According to FIG. 12, the suction amount increment is 2.65 L/min within a range of suction initiation (pressing amount=1.5 mm) to 2.0 mm in the first comparative example, and the suction amount rapidly increases compared to the suction amount increment of 0.56 L/min within the other range (pressing amount=2.5 mm to 3.0 mm). Within a range of half-pressing of the piston 61 (pressing amount=2.3 mm) to 3.0 mm, the suction amount increment is 0.83 L/min, which is small compared to the suction amount increment of 1.83 L/min within a range of 3.0 mm to 3.7 mm. In the first comparative example, a different of 1.0 L/min occurred at the same pressing amount range of 0.7 mm.

In the first example, in contrast, the V-shaped opening portion 70a communicates with the suction source connection port 57 within the range of the suction initiation to 2.0 mm, which is immediately after the suction initiation. Accordingly, the suction amount increment is suppressed to 2.0 L/min, and the rapid suction amount increase is addressed compared to the first comparative example. The difference between the suction amount increment of 1.55 L/min within a pressing amount range of 2.3 mm to 3.0 mm and the suction amount increment of 1.1 L/min within a range of 3.0 mm to 3.7 mm is 0.45 L/min, which is improved on the first comparative example. Accordingly, a change line of the suction amount with respect to the pressing amount, particularly, a change line from the suction initiation to the half-pressing of the piston 61, can be closer to the ideal line than in the first comparative example, and thus the operability is improved. For example, in a case where the suction amount is 2 L/min, the suction amount can be 2 L/min with a pressing amount that is closer to the ideal line than in the first comparative example. Also, neither the suctioning object clogging in the V-shaped opening portion 70a nor contrast agent attachment occurred. In addition, the arc-shaped opening portion 70 is formed to continue from the V-shaped opening portion 70a, and thus neither the suctioning object clogging in the one end portion of the outer peripheral surface opening 70 nor contrast agent attachment occur.

Results substantially identical to those of the first example were obtained after three tests under the same conditions as in the first example. Effects similar to those of the first example were obtained even in a case where the increment of the communication opening width at which the suction source connection port and the outer peripheral surface opening overlap with each other was three times the increment of the pressing stroke of the piston.

Even in the second example, the V-shaped opening portion communicates with the suction source connection port within the range of the suction initiation to 2.0 mm. Accordingly, the suction amount increment is suppressed to 1.32 L/min, and the rapid suction amount increase is addressed compared to the first comparative example. The difference between the suction amount increment of 1.83 L/min within the pressing amount range of 2.3 mm to 3.0 mm and the suction amount increment of 1.91 L/min within the range of 3.0 mm to 3.7 mm is 0.08 L/min, which is improved on the first comparative example. In addition, the suctioning object clogging in the V-shaped opening portion was slight, comparable to the first comparative example.

In the third example, the electronic endoscope in which the suction button 24 is incorporated was used as in the first example, and the contrast agent was suctioned from the treatment tool outlet 31 under the following conditions in confirming the operation of the suction button 24.

In the second comparative example, an electronic endoscope in which the suction button in which the inner peripheral surface of the first communication passage 72 is formed at a constant diameter to the other end of the piston is incorporated was used unlike in the third example in which the other end opening 71 has a tapered shape. The contrast agent was suctioned, as in the third example, from the suction conduit 32 under the following conditions in confirming the operation of the suction button.

The confirmation of the operation was performed as follows. First, the suction buttons of the third example and the second comparative example were in pressing operation to be in a suctioning state for one second. Then, a press release operation was repeated, and contrast agent-based suction button attachment initiation time and attachment termination time were measured three times each. The result in Table 1 was obtained as a result. The measurement condition was a suction pressure of the suction device of 40 kPa and Conray 60% (product name: manufactured by Daiichi Sankyo Co., Ltd.) was used as the contrast agent. The attachment initiation time means time of a case where return to the first position is less than three seconds, although delayed from press release, after the piston press release from the measurement initiation. From this attachment initiation time, time during which the sensitivity of the piston 61 being attached to the piston passage 53b affected by the contrast agent is present and the piston 61 is not smoothly operated is determined. Attachment termination time means time of a case where the return to the first position is further delayed to take at least three seconds after the piston press release. From the attachment termination time, time during which the piston 61 is not operated more smoothly is determined.

TABLE 1

| | | Attachment initiation time | Attachment termination time |
|---|---|---|---|
| Third example | 1 | 11 minutes | 31 minutes |
| | 2 | 7 minutes | 13 minutes |
| | 3 | 14 minutes | 20 minutes |
| Second comparative example | 1 | 2 minutes and 20 seconds | 6 minutes |
| | 2 | 3 minutes | 7 minutes |
| | 3 | 3 minutes | 8 minutes |

The measurement results of the third example and the second comparative example show that both the attachment initiation time and the attachment termination time of the third example are longer than those of the second comparative example and the adhesion between the piston 61 and the cylinder 53 is prevented.

In addition, the invention described in the following additional items can be apprehended from the above description.

[Additional Item 1]

A suction conduit switching apparatus for an endoscope, the suction conduit switching apparatus including: a cylinder that is disposed in a hand operation unit of the endoscope and has a piston passage which has one end that is open, a suction connection port which is formed at an other end of the piston passage and leads to a suction conduit, and a suction source connection port which is formed in an inner peripheral surface of the piston passage and leads to a suction source conduit; a piston that is inserted into the piston passage from the other end, one end protruding from the piston passage, and is displaced from a first position of a non-contact state to a second position by a pressing operation at the one end; a first communication passage that has an outer peripheral surface opening which is formed in an outer peripheral surface of the piston, communicates with the suction source connection port at the second position, and is blocked by an inner peripheral surface of the piston passage at the first position and the other end opening which is formed at the other end of the piston and communicates with the suction connection port, and allows the outer peripheral surface opening and the other end opening to communicate with each other; a second communication passage that has a circumferential groove which is formed in the outer peripheral surface of the piston, communicates with the suction source connection port at the first position, and is blocked by the inner peripheral surface of the piston passage at the second position and a notch passage which is formed from the circumferential groove to the one end of the piston in the outer peripheral surface of the piston, and allows the suction source connection port to communicate with an outside atmosphere via the circumferential groove and the notch passage; a rotation regulating unit that regulates rotation of the piston in the piston passage; and a residue relief section that is disposed in the other end opening and allows a residue which is suctioned from the suction conduit to be suctioned with ease.

[Additional Item 2]

The suction conduit switching apparatus for an endoscope according to additional item 1, wherein the residue relief section is formed into a tapered shape to be gradually reduced in diameter from the other end of the piston toward the one end of the piston.

[Additional Item 3]

The suction conduit switching apparatus for an endoscope according to additional item 1, wherein the residue relief section is a step portion in which the other end opening is formed to have an inner diameter larger than an inner diameter of the first communication passage.

[Additional Item 4]

The suction conduit switching apparatus for an endoscope according to additional item 1, wherein the residue relief section is a through-hole that penetrates the outer peripheral surface of the piston from the first communication passage at a position contiguous to the suction connection port.

[Additional Item 5]

The suction conduit switching apparatus for an endoscope according to any one of additional items 1 to 4, the suction conduit switching apparatus further including: a cylinder cap that is mounted on the cylinder and regulates separation of the piston from the one end of the piston passage; an operation cap that is disposed at the one end of the piston; and a spring that is disposed between the operation cap and the cylinder cap and biases the piston toward the cylinder cap, wherein the piston abuts against the cylinder cap and is stationary due to the biasing by the spring at the first position and the operation cap which is pushed down against the biasing by the spring abuts against the cylinder cap and is stationary at the second position.

[Additional Item 6]

The suction conduit switching apparatus for an endoscope according to additional item 5, wherein the cylinder cap integrally holds the piston and the spring and is detachably mounted on the cylinder.

[Additional Item 7]

An endoscope including: the conduit switching apparatus for an endoscope according to any one of additional items 1 to 6; and an insertion section that is inserted into a body, a hand operation unit that is disposed to be connected to the insertion section, a suction source conduit that is connected to a suction source, and a suction conduit that communicates with a suction port which is disposed in the insertion section.

According to effects of the invention described in the additional items above, the contrast agent that adheres between the piston and the piston passage can be decreased by the residue relief section which is disposed in the other end opening of the piston and the adhesion between the piston and the cylinder can be prevented.

What is claimed is:

1. A suction conduit switching apparatus for an endoscope, the suction conduit switching apparatus comprising:
a cylinder that is disposed in a hand operation unit of the endoscope, the cylinder comprising: a piston passage having one end that is open; a suction connection port which is formed at an other end of the piston passage and leads to a suction conduit; and a suction source connection port which is formed in an inner peripheral surface of the piston passage and leads to a suction source conduit;
a piston that is inserted into the cylinder with one end protruding from the piston passage, the piston being configured to be displaced from a first position to a second position by a pressing operation;
a first communication passage that comprises: an outer peripheral surface opening which is formed in an outer peripheral surface of the piston; and an other end opening which is formed at the other end of the piston, the outer peripheral surface opening being configured to communicate with the suction source connection port when the piston is at the second position, and to be blocked by an inner peripheral surface of the piston passage when the piston is at the first position, the other end opening being configured to communicate with the suction connection port, the outer peripheral surface opening and the other end opening being allowed to communicate with each other through the first communication passage;
a second communication passage that comprises: a circumferential groove which is formed in the outer peripheral surface of the piston; and a notch passage which is formed from the circumferential groove to the one end of the piston in the outer peripheral surface of the piston, the circumferential groove being configured to communicate with the suction source connection port when the piston is at the second position, and to be blocked by an inner peripheral surface of the piston passage when the piston is at the first position, the second communication passage allowing the suction source connection port to communicate with an outside atmosphere via the circumferential groove and the notch passage; and a rotation regulating unit that regulates rotation of the piston in the piston passage, wherein an increment of a communication opening width at which the suction source connection port and the outer peripheral surface opening overlap with each other is equal to or less than three times an increment of a pressing stroke of the piston when the piston is displaced from the first position to the second position by the pressing operation to the one end of the piston, and wherein at least one of the suction source connection port and the outer peripheral surface opening has a correction opening portion that has an opening width gradually increasing from the other end side toward the one end side.

2. A suction conduit switching apparatus for an endoscope, the suction conduit switching apparatus comprising:

a cylinder that is disposed in a hand operation unit of the endoscope, the cylinder comprising: a piston passage having one end that is open; a suction connection port which is formed at an other end of the piston passage and leads to a suction conduit; and a suction source connection port which is formed in an inner peripheral surface of the piston passage and leads to a suction source conduit;

a piston that is inserted into the cylinder with one end protruding from the piston passage, the piston being configured to be displaced from a first position to a second position by a pressing operation;

a first communication passage that comprises: an outer peripheral surface opening which is formed in an outer peripheral surface of the piston; and an other end opening which is formed at the other end of the piston, the outer peripheral surface opening being configured to communicate with the suction source connection port when the piston is at the second position, and to be blocked by an inner peripheral surface of the piston passage when the piston is at the first position, the other end opening being configured to communicate with the suction connection port, the outer peripheral surface opening and the other end opening being allowed to communicate with each other through the first communication passage;

a second communication passage that comprises: a circumferential groove which is formed in the outer peripheral surface of the piston; and a notch passage which is formed from the circumferential groove to the one end of the piston in the outer peripheral surface of the piston, the circumferential groove being configured to communicate with the suction source connection port when the piston is at the second position, and to be blocked by an inner peripheral surface of the piston passage when the piston is at the first position, the second communication passage allowing the suction source connection port to communicate with an outside atmosphere via the circumferential groove and the notch passage; and a rotation regulating unit that regulates rotation of the piston in the piston passage, wherein an increment of a communication opening width at which the suction source connection port and the outer peripheral surface opening overlap with each other is equal to or less than three times an increment of a pressing stroke of the piston when the piston is displaced from the first position to the second position by the pressing operation to the one end of the piston, wherein the increment of the communication opening width is equal to or more than 1.0 times and equal to or less than 2.5 times the increment of the pressing stroke of the piston when the piston is displaced from the first position to the second position by the pressing operation to the one end of the piston, and wherein at least one of the suction source connection port and the outer peripheral surface opening has a correction opening portion that has an opening width gradually increasing from the other end side toward the one end side.

3. A suction conduit switching apparatus for an endoscope, the suction conduit switching apparatus comprising:

a cylinder that is disposed in a hand operation unit of the endoscope, the cylinder comprising: a piston passage having one end that is open; a suction connection port which is formed at an other end of the piston passage and leads to a suction conduit; and a suction source connection port which is formed in an inner peripheral surface of the piston passage and leads to a suction source conduit;

a piston that is inserted into the cylinder with one end protruding from the piston passage, the piston being configured to be displaced from a first position to a second position by a pressing operation;

a first communication passage that comprises: an outer peripheral surface opening which is formed in an outer peripheral surface of the piston; and an other end opening which is formed at the other end of the piston, the outer peripheral surface opening being configured to communicate with the suction source connection port when the piston is at the second position, and to be blocked by an inner peripheral surface of the piston passage when the piston is at the first position, the other end opening being configured to communicate with the suction connection port, the outer peripheral surface opening and the other end opening being allowed to communicate with each other through the first communication passage;

a second communication passage that comprises: a circumferential groove which is formed in the outer peripheral surface of the piston; and a notch passage which is formed from the circumferential groove to the one end of the piston in the outer peripheral surface of the piston, the circumferential groove being configured to communicate with the suction source connection port when the piston is at the second position, and to be blocked by an inner peripheral surface of the piston passage when the piston is at the first position, the second communication passage allowing the suction source connection port to communicate with an outside atmosphere via the circumferential groove and the notch passage; and a rotation regulating unit that regulates rotation of the piston in the piston passage, wherein an increment of a communication opening width at which the suction source connection port and the outer peripheral surface opening overlap with each other is equal to or less than three times an increment of a pressing stroke of the piston when the piston is displaced from the first position to the second position by the pressing operation to the one end of the piston, wherein at least one of the suction source connection port and the outer peripheral surface opening has a correction opening portion that has an opening width gradually increasing from the other end side toward the one end side, and wherein one of the suction source connection port and the outer peripheral surface opening has a rectangular shape, and the other one of the suction source connection port and the outer peripheral surface opening has the V-shaped correction opening portion at a part starting to communicate with the one of the suction source connection port and the outer peripheral surface opening in response to pressing of the piston.

4. A suction conduit switching apparatus for an endoscope, the suction conduit switching apparatus comprising:

a cylinder that is disposed in a hand operation unit of the endoscope, the cylinder comprising: a piston passage having one end that is open; a suction connection port which is formed at an other end of the piston passage and leads to a suction conduit; and a suction source connection port which is formed in an inner peripheral surface of the piston passage and leads to a suction source conduit;

a piston that is inserted into the cylinder with one end protruding from the piston passage, the piston being configured to be displaced from a first position to a second position by a pressing operation;

a first communication passage that comprises: an outer peripheral surface opening which is formed in an outer peripheral surface of the piston; and an other end opening which is formed at the other end of the piston, the outer peripheral surface opening being configured to communicate with the suction source connection port when the piston is at the second position, and to be blocked by an inner peripheral surface of the piston passage when the piston is at the first position, the other end opening being configured to communicate with the suction connection port, the outer peripheral surface opening and the other end opening being allowed to communicate with each other through the first communication passage;

a second communication passage that comprises: a circumferential groove which is formed in the outer peripheral surface of the piston; and a notch passage which is formed from the circumferential groove to the one end of the piston in the outer peripheral surface of the piston, the circumferential groove being configured to communicate with the suction source connection port when the piston is at the second position, and to be blocked by an inner peripheral surface of the piston passage when the piston is at the first position, the second communication passage allowing the suction source connection port to communicate with an outside atmosphere via the circumferential groove and the notch passage; and a rotation regulating unit that regulates rotation of the piston in the piston passage, wherein an increment of a communication opening width at which the suction source connection port and the outer peripheral surface opening overlap with each other is equal to or less than three times an increment of a pressing stroke of the piston when the piston is displaced from the first position to the second position by the pressing operation to the one end of the piston, wherein the increment of the communication opening width is equal to or more than 1.0 times and equal to or less than 2.5 times the increment of the pressing stroke of the piston when the piston is displaced from the first position to the second position by the pressing operation to the one end of the piston, wherein at least one of the suction source connection port and the outer peripheral surface opening has a correction opening portion that has an opening width gradually increasing from the other end side toward the one end side, and wherein one of the suction source connection port and the outer peripheral surface opening has a rectangular shape, and the other one of the suction source connection port and the outer peripheral surface opening has the V-shaped correction opening portion at a part starting to communicate with the one of the suction source connection port and the outer peripheral surface opening in response to pressing of the piston.

5. A suction conduit switching apparatus for an endoscope, the suction conduit switching apparatus comprising:

a cylinder that is disposed in a hand operation unit of the endoscope, the cylinder comprising: a piston passage having one end that is open; a suction connection port which is formed at an other end of the piston passage and leads to a suction conduit; and a suction source connection port which is formed in an inner peripheral surface of the piston passage and leads to a suction source conduit;

a piston that is inserted into the cylinder with one end protruding from the piston passage, the piston being configured to be displaced from a first position to a second position by a pressing operation;

a first communication passage that comprises: an outer peripheral surface opening which is formed in an outer peripheral surface of the piston; and an other end opening which is formed at the other end of the piston, the outer peripheral surface opening being configured to communicate with the suction source connection port when the piston is at the second position, and to be blocked by an inner peripheral surface of the piston passage when the piston is at the first position, the other end opening being configured to communicate with the suction connection port, the outer peripheral surface opening and the other end opening being allowed to communicate with each other through the first communication passage;

a second communication passage that comprises: a circumferential groove which is formed in the outer peripheral surface of the piston; and a notch passage which is formed from the circumferential groove to the one end of the piston in the outer peripheral surface of the piston, the circumferential groove being configured to communicate with the suction source connection port when the piston is at the second position, and to be blocked by an inner peripheral surface of the piston passage when the piston is at the first position, the second communication passage allowing the suction source connection port to communicate with an outside atmosphere via the circumferential groove and the notch passage; and a rotation regulating unit that regulates rotation of the piston in the piston passage, wherein an increment of a communication opening width at which the suction source connection port and the outer peripheral surface opening overlap with each other is equal to or less than three times an increment of a pressing stroke of the piston when the piston is displaced from the first position to the second position by the pressing operation to the one end of the piston, wherein at least one of the suction source connection port and the outer peripheral surface opening has a correction opening portion that has an opening width gradually increasing from the other end side toward the one end side, wherein one of the suction source connection port and the outer peripheral surface opening has a rectangular shape, and the other one of the suction source connection port and the outer peripheral surface opening has the V-shaped correction opening portion at a part starting to communicate with the one of the suction source connection port and the outer peripheral surface opening in response to pressing of the piston, and wherein the other one of the suction source connection port and the outer peripheral surface opening has an arc-shaped opening portion that continues from the correction opening portion.

6. A suction conduit switching apparatus for an endoscope, the suction conduit switching apparatus comprising:
a cylinder that is disposed in a hand operation unit of the endoscope, the cylinder comprising: a piston passage having one end that is open; a suction connection port which is formed at an other end of the piston passage and leads to a suction conduit; and a suction source connection port which is formed in an inner peripheral surface of the piston passage and leads to a suction source conduit;
a piston that is inserted into the cylinder with one end protruding from the piston passage, the piston being configured to be displaced from a first position to a second position by a pressing operation;
a first communication passage that comprises: an outer peripheral surface opening which is formed in an outer peripheral surface of the piston; and an other end opening which is formed at the other end of the piston, the outer peripheral surface opening being configured to communicate with the suction source connection port when the piston is at the second position, and to be blocked by an inner peripheral surface of the piston passage when the piston is at the first position, the other end opening being configured to communicate with the suction connection port, the outer peripheral surface opening and the other end opening being allowed to communicate with each other through the first communication passage;
a second communication passage that comprises: a circumferential groove which is formed in the outer peripheral surface of the piston; and a notch passage which is formed from the circumferential groove to the one end of the piston in the outer peripheral surface of the piston, the circumferential groove being configured to communicate with the suction source connection port when the piston is at the second position, and to be blocked by an inner peripheral surface of the piston passage when the piston is at the first position, the second communication passage allowing the suction source connection port to communicate with an outside atmosphere via the circumferential groove and the notch passage; and
a rotation regulating unit that regulates rotation of the piston in the piston passage,
wherein an increment of a communication opening width at which the suction source connection port and the outer peripheral surface opening overlap with each other is equal to or less than three times an increment of a pressing stroke of the piston when the piston is displaced from the first position to the second position by the pressing operation to the one end of the piston, wherein the increment of the communication opening width is equal to or more than 1.0 times and equal to or less than 2.5 times the increment of the pressing stroke of the piston when the piston is displaced from the first position to the second position by the pressing operation to the one end of the piston, wherein at least one of the suction source connection port and the outer peripheral surface opening has a correction opening portion that has an opening width gradually increasing from the other end side toward the one end side, wherein one of the suction source connection port and the outer peripheral surface opening has a rectangular shape, and the other one of the suction source connection port and the outer peripheral surface opening has the V-shaped correction opening portion at a part starting to communicate with the one of the suction source connection port and the outer peripheral surface opening in response to pressing of the piston, and wherein the other one of the suction source connection port and the outer peripheral surface opening has an arc-shaped opening portion that continues from the correction opening portion.

7. A suction conduit switching apparatus for an endoscope, the suction conduit switching apparatus comprising:
a cylinder that is disposed in a hand operation unit of the endoscope, the cylinder comprising: a piston passage having one end that is open; a suction connection port which is formed at an other end of the piston passage and leads to a suction conduit; and a suction source connection port which is formed in an inner peripheral surface of the piston passage and leads to a suction source conduit;
a piston that is inserted into the cylinder with one end protruding from the piston passage, the piston being configured to be displaced from a first position to a second position by a pressing operation;
a first communication passage that comprises: an outer peripheral surface opening which is formed in an outer peripheral surface of the piston; and an other end opening which is formed at the other end of the piston, the outer peripheral surface opening being configured to communicate with the suction source connection port when the piston is at the second position, and to be blocked by an inner peripheral surface of the piston passage when the piston is at the first position, the other end opening being configured to communicate with the suction connection port, the outer peripheral surface opening and the other end opening being allowed to communicate with each other through the first communication passage;
a second communication passage that comprises: a circumferential groove which is formed in the outer peripheral surface of the piston; and a notch passage which is formed from the circumferential groove to the one end of the piston in the outer peripheral surface of the piston, the circumferential groove being configured to communicate with the suction source connection port when the piston is at the second position, and to be blocked by an inner peripheral surface of the piston passage when the piston is at the first position, the second communication passage allowing the suction source connection port to communicate with an outside atmosphere via the circumferential groove and the notch passage; and a rotation regulating unit that regulates rotation of the piston in the piston passage, wherein an increment of a communication opening width at which the suction source connection port and the outer peripheral surface opening overlap with each other is equal to or less than three times an increment of a pressing stroke of the piston when the piston is displaced from the first position to the second position by the pressing operation to the one end of the piston, wherein at least one of the suction source connection port and the outer peripheral surface opening has a correction opening portion that has an opening width gradually increasing from the other end side toward the one end side, and wherein the outer peripheral surface opening is smaller than the suction source connection port.

8. A suction conduit switching apparatus for an endoscope, the suction conduit switching apparatus comprising:

a cylinder that is disposed in a hand operation unit of the endoscope, the cylinder comprising: a piston passage having one end that is open; a suction connection port which is formed at an other end of the piston passage and leads to a suction conduit; and a suction source connection port which is formed in an inner peripheral surface of the piston passage and leads to a suction source conduit;

a piston that is inserted into the cylinder with one end protruding from the piston passage, the piston being configured to be displaced from a first position to a second position by a pressing operation;

a first communication passage that comprises: an outer peripheral surface opening which is formed in an outer peripheral surface of the piston; and an other end opening which is formed at the other end of the piston, the outer peripheral surface opening being configured to communicate with the suction source connection port when the piston is at the second position, and to be blocked by an inner peripheral surface of the piston passage when the piston is at the first position, the other end opening being configured to communicate with the suction connection port, the outer peripheral surface opening and the other end opening being allowed to communicate with each other through the first communication passage;

a second communication passage that comprises: a circumferential groove which is formed in the outer peripheral surface of the piston; and a notch passage which is formed from the circumferential groove to the one end of the piston in the outer peripheral surface of the piston, the circumferential groove being configured to communicate with the suction source connection port when the piston is at the second position, and to be blocked by an inner peripheral surface of the piston passage when the piston is at the first position, the second communication passage allowing the suction source connection port to communicate with an outside atmosphere via the circumferential groove and the notch passage; and a rotation regulating unit that regulates rotation of the piston in the piston passage, wherein an increment of a communication opening width at which the suction source connection port and the outer peripheral surface opening overlap with each other is equal to or less than three times an increment of a pressing stroke of the piston when the piston is displaced from the first position to the second position by the pressing operation to the one end of the piston, and wherein an inclined notch is formed in the outer peripheral surface of the piston, which inclined notch continues from the circumferential groove on the other end side of the piston rather than the circumferential groove, communicates with the suction source connection port at the first position, and faces the inner peripheral surface of the piston passage at the second position.

9. A suction conduit switching apparatus for an endoscope, the suction conduit switching apparatus comprising:

a cylinder that is disposed in a hand operation unit of the endoscope, the cylinder comprising: a piston passage having one end that is open; a suction connection port which is formed at an other end of the piston passage and leads to a suction conduit; and a suction source connection port which is formed in an inner peripheral surface of the piston passage and leads to a suction source conduit;

a piston that is inserted into the cylinder with one end protruding from the piston passage, the piston being configured to be displaced from a first position to a second position by a pressing operation;

a first communication passage that comprises: an outer peripheral surface opening which is formed in an outer peripheral surface of the piston; and an other end opening which is formed at the other end of the piston, the outer peripheral surface opening being configured to communicate with the suction source connection port when the piston is at the second position, and to be blocked by an inner peripheral surface of the piston passage when the piston is at the first position, the other end opening being configured to communicate with the suction connection port, the outer peripheral surface opening and the other end opening being allowed to communicate with each other through the first communication passage;

a second communication passage that comprises: a circumferential groove which is formed in the outer peripheral surface of the piston; and a notch passage which is formed from the circumferential groove to the one end of the piston in the outer peripheral surface of the piston, the circumferential groove being configured to communicate with the suction source connection port when the piston is at the second position, and to be blocked by an inner peripheral surface of the piston passage when the piston is at the first position, the second communication passage allowing the suction source connection port to communicate with an outside atmosphere via the circumferential groove and the notch passage; and a rotation regulating unit that regulates rotation of the piston in the piston passage, wherein an increment of a communication opening width at which the suction source connection port and the outer peripheral surface opening overlap with each other is equal to or less than three times an increment of a pressing stroke of the piston when the piston is displaced from the first position to the second position by the pressing operation to the one end of the piston, wherein the increment of the communication opening width is equal to or more than 1.0 times and equal to or less than 2.5 times the increment of the pressing stroke of the piston when the piston is displaced from the first position to the second position by the pressing operation to the one end of the piston, and wherein an inclined notch is formed in the outer peripheral surface of the piston, which inclined notch continues from the circumferential groove on the other end side of the piston rather than the circumferential groove, communicates with the suction source connection port at the first position, and faces the inner peripheral surface of the piston passage at the second position.

10. A suction conduit switching apparatus for an endoscope, the suction conduit switching apparatus comprising:

a cylinder that is disposed in a hand operation unit of the endoscope, the cylinder comprising: a piston passage having one end that is open; a suction connection port which is formed at an other end of the piston passage and leads to a suction conduit; and a suction source connection port which is formed in an inner peripheral surface of the piston passage and leads to a suction source conduit;

a piston that is inserted into the cylinder with one end protruding from the piston passage, the piston being configured to be displaced from a first position to a second position by a pressing operation;

a first communication passage that comprises: an outer peripheral surface opening which is formed in an outer peripheral surface of the piston; and an other end opening which is formed at the other end of the piston, the outer peripheral surface opening being configured to communicate with the suction source connection port when the piston is at the second position, and to be blocked by an inner peripheral surface of the piston passage when the piston is at the first position, the other end opening being configured to communicate with the suction connection port, the outer peripheral surface opening and the other end opening being allowed to communicate with each other through the first communication passage;

a second communication passage that comprises: a circumferential groove which is formed in the outer peripheral surface of the piston; and a notch passage which is formed from the circumferential groove to the one end of the piston in the outer peripheral surface of the piston, the circumferential groove being configured to communicate with the suction source connection port when the piston is at the second position, and to be blocked by an inner peripheral surface of the piston passage when the piston is at the first position, the second communication passage allowing the suction source connection port to communicate with an outside atmosphere via the circumferential groove and the notch passage; and a rotation regulating unit that regulates rotation of the piston in the piston passage, wherein an increment of a communication opening width at which the suction source connection port and the outer peripheral surface opening overlap with each other is equal to or less than three times an increment of a pressing stroke of the piston when the piston is displaced from the first position to the second position by the pressing operation to the one end of the piston, wherein at least one of the suction source connection port and the outer peripheral surface opening has a correction opening portion that has an opening width gradually increasing from the other end side toward the one end side, and wherein an inclined notch is formed in the outer peripheral surface of the piston, which inclined notch continues from the circumferential groove on the other end side of the piston rather than the circumferential groove, communicates with the suction source connection port at the first position, and faces the inner peripheral surface of the piston passage at the second position.

11. A suction conduit switching apparatus for an endoscope, the suction conduit switching apparatus comprising:

a cylinder that is disposed in a hand operation unit of the endoscope, the cylinder comprising: a piston passage having one end that is open; a suction connection port which is formed at an other end of the piston passage and leads to a suction conduit; and a suction source connection port which is formed in an inner peripheral surface of the piston passage and leads to a suction source conduit;

a piston that is inserted into the cylinder with one end protruding from the piston passage, the piston being configured to be displaced from a first position to a second position by a pressing operation;

a first communication passage that comprises: an outer peripheral surface opening which is formed in an outer peripheral surface of the piston; and an other end opening which is formed at the other end of the piston, the outer peripheral surface opening being configured to communicate with the suction source connection port when the piston is at the second position, and to be blocked by an inner peripheral surface of the piston passage when the piston is at the first position, the other end opening being configured to communicate with the suction connection port, the outer peripheral surface opening and the other end opening being allowed to communicate with each other through the first communication passage;

a second communication passage that comprises: a circumferential groove which is formed in the outer peripheral surface of the piston; and a notch passage which is formed from the circumferential groove to the one end of the piston in the outer peripheral surface of the piston, the circumferential groove being configured to communicate with the suction source connection port when the piston is at the second position, and to be blocked by an inner peripheral surface of the piston passage when the piston is at the first position, the second communication passage allowing the suction source connection port to communicate with an outside atmosphere via the circumferential groove and the notch passage; and a rotation regulating unit that regulates rotation of the piston in the piston passage, wherein an increment of a communication opening width at which the suction source connection port and the outer peripheral surface opening overlap with each other is equal to or less than three times an increment of a pressing stroke of the piston when the piston is displaced from the first position to the second position by the pressing operation to the one end of the piston, wherein an inclined notch is formed in the outer peripheral surface of the piston, which inclined notch continues from the circumferential groove on the other end side of the piston rather than the circumferential groove, communicates with the suction source connection port at the first position, and faces the inner peripheral surface of the piston passage at the second position, and wherein the inclined notch is formed in a direction in which a suction source connection passage that communicates with the suction source connection port extends.

12. A suction conduit switching apparatus for an endoscope, the suction conduit switching apparatus comprising:
- a cylinder that is disposed in a hand operation unit of the endoscope, the cylinder comprising: a piston passage having one end that is open; a suction connection port which is formed at an other end of the piston passage and leads to a suction conduit; and a suction source connection port which is formed in an inner peripheral surface of the piston passage and leads to a suction source conduit;
- a piston that is inserted into the cylinder with one end protruding from the piston passage, the piston being configured to be displaced from a first position to a second position by a pressing operation;
- a first communication passage that comprises: an outer peripheral surface opening which is formed in an outer peripheral surface of the piston; and an other end opening which is formed at the other end of the piston, the outer peripheral surface opening being configured to communicate with the suction source connection port when the piston is at the second position, and to be blocked by an inner peripheral surface of the piston passage when the piston is at the first position, the other end opening being configured to communicate with the suction connection port, the outer peripheral surface opening and the other end opening being allowed to communicate with each other through the first communication passage;
- a second communication passage that comprises: a circumferential groove which is formed in the outer peripheral surface of the piston; and a notch passage which is formed from the circumferential groove to the one end of the piston in the outer peripheral surface of the piston, the circumferential groove being configured to communicate with the suction source connection port when the piston is at the second position, and to be blocked by an inner peripheral surface of the piston passage when the piston is at the first position, the second communication passage allowing the suction source connection port to communicate with an outside atmosphere via the circumferential groove and the notch passage;
- a rotation regulating unit that regulates rotation of the piston in the piston passage;
- a cylinder cap that is mounted on the cylinder and regulates separation of the piston from the one end of the piston passage;
- an operation cap that is disposed at the one end of the piston; and
- a spring that is disposed between the operation cap and the cylinder cap and biases the piston toward the cylinder cap, wherein an increment of a communication opening width at which the suction source connection port and the outer peripheral surface opening overlap with each other is equal to or less than three times an increment of a pressing stroke of the piston when the piston is displaced from the first position to the second position by the pressing operation to the one end of the piston, wherein at least one of the suction source connection port and the outer peripheral surface opening has a correction opening portion that has an opening width gradually increasing from the other end side toward the one end side, and wherein the piston is stationary at the first position as abutting against the cylinder cap due to biasing by the spring, and the piston is stationary at the second position with the operation cap which is pushed down against the biasing by the spring abutting against the cylinder cap.

* * * * *